United States Patent
Herrmann et al.

(10) Patent No.: US 10,590,202 B2
(45) Date of Patent: *Mar. 17, 2020

(54) RECOMBINANT BISPECIFIC ANTIBODY BINDING TO CD20 AND CD95

(71) Applicant: Baliopharm AG, Basel (CH)

(72) Inventors: Andreas Herrmann, Pfeffingen (CH); Ludger Grosse-Hovest, Tübingen (DE)

(73) Assignee: BALIOPHARM AG, Basel (CH)

( * ) Notice: Subject to any disclaimer, the term of this patent is extended or adjusted under 35 U.S.C. 154(b) by 522 days.

This patent is subject to a terminal disclaimer.

(21) Appl. No.: 14/443,752

(22) PCT Filed: Nov. 19, 2013

(86) PCT No.: PCT/EP2013/074142
§ 371 (c)(1),
(2) Date: May 19, 2015

(87) PCT Pub. No.: WO2014/076292
PCT Pub. Date: May 22, 2014

(65) Prior Publication Data
US 2015/0274833 A1   Oct. 1, 2015

(30) Foreign Application Priority Data
Nov. 19, 2012 (EP) .................... 12193196

(51) Int. Cl.
*C07K 16/28* (2006.01)
*A61K 39/00* (2006.01)

(52) U.S. Cl.
CPC ...... *C07K 16/2887* (2013.01); *C07K 16/2878* (2013.01); *A61K 2039/505* (2013.01); *C07K 2317/24* (2013.01); *C07K 2317/31* (2013.01); *C07K 2317/51* (2013.01); *C07K 2317/515* (2013.01); *C07K 2317/524* (2013.01); *C07K 2317/55* (2013.01); *C07K 2317/565* (2013.01); *C07K 2317/622* (2013.01); *C07K 2317/64* (2013.01); *C07K 2317/73* (2013.01); *C07K 2317/92* (2013.01); *C07K 2319/00* (2013.01)

(58) Field of Classification Search
CPC ............ C07K 16/2887; C07K 16/2878; C07K 2317/622; C07K 2319/00; C07K 2317/64; C07K 2317/73; C07K 2317/92; C07K 2317/565; C07K 2317/515; C07K 2317/51; C07K 2317/53; C07K 2317/55; C07K 2317/524; C07K 2317/31; C07K 2317/24; A61K 2039/505
See application file for complete search history.

(56) References Cited

U.S. PATENT DOCUMENTS 8,058,399 B2   11/2011  Jung
9,718,893 B2 *  8/2017  Jung .................. C07K 16/2803
2003/0232049 A1 * 12/2003  Jung et al. ............. C07K 16/28
                                                   424/143.1
2006/0099662 A1 *  5/2006  Chuntharapai et al. .....................
                                                   C07K 16/2896
                                                   435/7.92
2012/0244163 A1 *  9/2012  Schoeberl et al. .........................
                                                   C07K 16/2863
                                                   424/136.1

FOREIGN PATENT DOCUMENTS

| CA | 2416572 A1 | 1/2002 |
| CN | 102250247 A | 11/2011 |
| WO | 0228904 A2 | 4/2002 |
| WO | 02066516 A2 | 8/2002 |
| WO | 2004056312 A2 | 7/2004 |
| WO | 2005044306 A2 | 5/2005 |
| WO | 2012/065055 A2 | 5/2012 |
| WO | 2013072523 A1 * | 5/2013 |
| WO | 2013092001 A1 | 6/2013 |
| WO | 2014076292 A1 | 5/2014 |

OTHER PUBLICATIONS

Lu et al., "Fab-scFv fusion protein: an efficient approach to production of bispecific antibody fragments", Journal of Immunological Methods, 267 (2002) 213-226.*
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, 2002, 169: 3076-3084.*
MacCallumm et al., "Antibody-antigen Interactions: Contact Analysis and Binding Site Topography", J. Mo/. Biol. (1996) 262, 732-745.*
Gong et al., "Engineered Human Antibody Constant Domains with Increased Stability", J. Biol. Chem. 284:14203-14210, 2009 (Year: 2009).*
Lloyd et al., Protein Engineering, Design & Selection 22:159-168 (Year: 2009).*
Edwards et al., J Mol Biol. 334(1): 103-118 (Year: 2003).*
Rudikoff et al., Proc. Natl. Acad. Sci. USA vol. 79 p. 1979-1983 (Year: 1982).*
Silverman, G. J. Anti-CD20 Therapy and Autoimmune Disease: Therapeutic opportunities and evolving insights. Frontiers in bioscience 12, 2194-2206, Jan. 1, 2007.
Herrmann T. et al. "Construction of Optimized Bispecific Antibodies for Selective Activation of the Death Receptor CD95", Cancer Research, vol. 68, No. 4, Feb. 15, 2008 pp. 1221-1227.
Jung, G. et al. "Target Cell-restricted Triggering of the CD95 (APO-1/Fas) Death Receptor with Bispecific Antibody Fragments", Cancer Research, vol. 61, Mar. 1, 2001, pp. 1846-1848.

(Continued)

*Primary Examiner* — Phuong Huynh
(74) *Attorney, Agent, or Firm* — Meunier Carlin & Curfman LLC

(57) ABSTRACT

A bispecific antibody format, which comprises a) a Fab fragment comprising a first binding site for a first antigen; b) an scFv fragment comprising a second binding site for a second antigen; and c) a CH2 domain, wherein the Fab fragment and the scFv fragment are linked via the CH2 domain, wherein the first antigen is CD95 and the second antigen is CD20; or the first antigen is CD20 and the second antigen is CD95.

10 Claims, 13 Drawing Sheets

Figure 1:
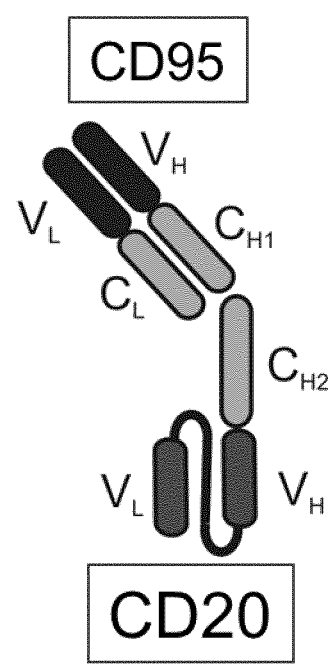

Specification includes a Sequence Listing.

(56) References Cited

OTHER PUBLICATIONS

Nalivaiko, K. et al. "Inhibition of Antibody Production in Vitro with Bispecific CD20 × CD95 Antibodies", Blood, vol. 118, No. 21, Nov. 2011, pp. 510.

Otz, T. et al. "Target Cell-restricted Stimulation of the CD95 (Apo-1/Fas) Death Receptor with Various Bispecific CD20XCD95 Antibodies", Advanced in Experimental Medicine and Biology, vol. 691, Jan. 1, 2011, pp. 797-798.

Clark et al. 2005. "How does B cell depletion therapy work, and how can it be improved?" Ann Rheum Dis 64: iv77-iv80.

Cohen, Stanley B., et al. "Rituximab for rheumatoid arthritis refractory to anti-tumor necrosis factor therapy: results of a multicenter, randomized, double-blind, placebo-controlled, phase III trial evaluating primary efficacy and safety at twenty-four weeks." Arthritis & Rheumatism 54.9 (2006): 2793-2806.

Colman, Peter M. "Effects of amino acid sequence changes on antibody-antigen interactions." Research in Immunology 145.1 (1994): 33-36.

Edwards, J. C. W., and G. Cambridge. "Sustained improvement in rheumatoid arthritis following a protocol designed to deplete B lymphocytes." Rheumatology 40.2 (2001): 205-211.

Emery, Paul, et al. "The efficacy and safety of rituximab in patients with active rheumatoid arthritis despite methotrexate treatment: results of a phase IIB randomized, double-blind, placebo-controlled, dose-ranging trial." Arthritis & Rheumatism 54.5 (2006): 1390-1400.

Huck, Sylvie, et al. "High-density expression of CD95 on B cells and underrepresentation of the B-1 cell subset in human lupus." Journal of autoimmunity 11.5 (1998): 449-455.

Jung et al. (1991). Target cell-induced T cell activation with bi- and trispecific antibody fragments. Eur J Immunol, 21, 2431-2435.

Lens, S. M., et al. "A dual role for both CD40-ligand and TNF-alpha in controlling human B cell death." The Journal of Immunology 156.2 (1996): 507-514.

Ping, L. et al. (2005). Novel role of CD40 in Fas-dependent apoptosis of cultured salivary epithelial cells from patients with Sjögren's syndrome. Arthritis & Rheumatism, 52(2), 573-581.

Ricci-Vitiani, L., et al. "CD95/CD95L interactions and their role in autoimmunity." Apoptosis 5.5 (2000): 419-424.

Rudikoff, Stuart, et al. "Single amino acid substitution altering antigen-binding specificity." Proceedings of the National Academy of Sciences 79.6 (1982): 1979-1983.

Wang, J. et al. (2004). The role of pathogenic B-cell clones in antibody mediated autoimmune disorders. Journal of Dermatological Science, 36(3), 141-148.

Wischhusen, J. et al. (2005). Death receptor-mediated apoptosis in human malignant glioma cells: modulation by the CD40/CD40L system. Journal of neuroimmunology, 162(1), 28-42.

Yonehara, S. (2002). Death receptor Fas and autoimmune disease: from the original generation to therapeutic application of agonistic anti-Fas monoclonal antibody. Cytokine & growth factor reviews, 13(4), 393-402.

Tobon, et al., "B cell-targeted therapies in Sjogren's syndrome", Autoimmunity Reviews 9, 2010, 224-228.

Bosma, Gayle C. et al., A severe combined immunodeficiency mutation in the mouse, Nature vol. 301, No. 5900, Feb. 10, 1983, pp. 527-530.

Lifely, M. Robert et al., "Glycosylation and biological activity of CAMPATH-1H expressed in different cell lines and grown under different culture conditions", Glycobiology vol. 5 No. 8, pp. 813-822, 1995.

Liu, Alvin Y. et al., "Production of a Mouse-Human Chimeric Monoclonal Antibody to CD20 With Potent Fc-Dependent Biological Activity", The Journal of Immunology, vol. 139, No. 10, pp. 3521-3526, Nov. 15, 1987.

Office Action issued in Chinese Application No. 201380069135.7, dated Jan. 5, 2018.

* cited by examiner

Fig. 2:

Fig. 2A: murine sequences of an anti-CD95 antibody (Apo-1)

\>APO-VL
mouse kappa subgroup III

SEQ ID 1:
DIVLTQSPASLAVSLGQRATISCRASESVEYYGTSLMQWYQQKPGQPPKLLIYVASNVES
GVPARFSGSGSGTDFSLNIHPVEEDDIAMYFCQQSTKVPWTFGGGTKLEIKR

CDR-L1: RASESVEYYGTSLMQ (SEQ ID 2)
CDR-L2: VASNVES (SEQ ID 3)
CDR-L3: QQSTKVPWT (SEQ ID 4)

\>APO-VH
mouse heavy subgroup IIId

SEQ ID 5:
EVQLVETGGGLVQPKGSLKLSCAASGFTFNTNAMNWVRQAPGKGLEWVARIRSKSNNYAT
YYAESVKDRFTISRDDSQSMLYLQMNNLKAEDTAMYYCVTDGYYWGQGTTLTVSS

CDR-H1: TNAMN (SEQ ID 6)
CDR-H2: RIRSKSNNYATYYAESVKD (SEQ ID 7)
CDR-H3: DGYY (SEQ ID 8)

Fig. 2B: humanisedsequences of an anti-CD95 antibody (Apo-1)

\>humApo-VL
human kappa subgroup IV

SEQ ID 9:
DIVMTQSPDSLAVSLGERATISCRASESVEYYGTSLMQWYQQKPGQPPKLLIYVASNVES
GVPDRFSGSGSGTDFTLTISSLQAEDVAVYFCQQSTKVPWTFGQGTKLEIK

\>humApo-VH
human subgroup III

SEQ ID 10:
EVQLVESGGGLVKPGGSLRLSCAASGFTFNTNAMNWVRQAPGKGLEWVARIRSKSNNYAT
YYAESVKDRFTISRDDSKNTLYLQMNSLKTEDTAVYYCVTDGYYWGQGTTLTVSS

Fig. 2C: murine sequences anti-CD20 antibody

>CD20-VL (accession # M17953)
mouse kappa subgroup VI

SEQ ID 11:
DIVLSQSPAILSASPGEKVTMTCRASSSVSYMHWYQQKPGSSPKPWIYAPSNLASGVPARFS
GSGSGTSYSLTISRVEAEDAATYYCQQWSFNPPTFGAGTKLELK

CDR-L1: RASSSVSYM (SEQ ID 12)
CDR-L2: APSNLAS (SEQ ID 13)
CDR-L3: QQWSFNPPT (SEQ ID 14)

>CD20-VH (accession # M17954)
mouse heavy subgroup IIb

SEQ ID 15:
QAYLQQSGAELVRPGASVKMSCKASGYTFTSYNMHWVKQTPRQGLEWIGAIYPGNGDTSYNQK
FKGKATLTVDKSSSTAYMQLSSLTSEDSAVYFCARVVYYSNSYWYFDVWGTGTTVTVSS

CDR-H1: SYNMH (SEQ ID 16)
CDR-H2: AIYPGNGDTSYNQKFKG (SEQ ID 17)
CDR-H3: VVYYSNSYWYFDV (SEQ ID 18)

Fig. 2D: humanised sequences anti-CD20 antibody

>humCD20-VL
human kappa subgroup I

SEQ ID 19:
DIQMTQSPSSLSASVGDRVTITCRASSSVSYMHWYQQKPGKAPKPLIYAPSNLASGVPSRFS
GSGSGTDFTLTISSLQPEDFATYYCQQWSFNPPTFGQGTKLEIK

>humCD20-VH
human subgroup I

SEQ ID 20:
QVQLVQSGAEVKKPGASVKVSCKASGYTFTSYNMHWVRQAPGQGLEWIGAIYPGNGDTSYNQK
FKGRVTITRDTSASTAYMELSSLRSEDTAVYYCARVVYYSNSYWYFDVWGQGTLVTVSS

Fig. 2E: Bispecific antibody CD95xCD20 (bsFabXsc-format, depicted in Fig.1)

i) chimeric versions light-chain (chimeric version):

CD95-VJ + human CL (kappa); chimeric light chain w/o leader peptide

SEQ ID 21:
```
1        DIVLTQSPAS  LAVSLGQRAT  ISCRASESVE  YYGTSLMQWY  QQKPGQPPKL
51   LIYVASNVES  GVPARFSGSG  SGTDFSLNIH  PVEEDDIAMY  FCQQSTKVPW
101  TFGGGTKLEI  KRTVAAPSVF  IFPPSDEQLK  SGTASVVCLL  NNFYPREAKV
151       QWKVDNALQS  GNSQESVTEQ  DSKDSTYSLS  STLTLSKADY  EKHKVYACEV
201  THQGLSSPVT  KSFNRGEC*
```

Amino acid 1-111: anti-CD95 VJ (mouse)
underlined: human constant kappa chain

Nucleotide sequence (SEQ ID 22):

```
GACATTGTGCTCACCCAATCTCCAGCTTCTTTGGCTGTGTCTCTAGGGCAGAGAGCCACC
ATCTCCTGCAGAGCCAGTGAAAGTGTTGAATATTATGGCACAAGTTTAATGCAATGGTAC
CAACAGAAGCCAGGACAGCCACCCAAACTCCTCATCTATGTTGCATCCAACGTAGAATCT
GGGGTCCCTGCCAGGTTTAGTGGCAGTGGGTCTGGGACAGACTTCAGCCTCAACATCCAC
CCTGTGGAGGAGGATGATATTGCAATGTATTTCTGTCAGCAAAGTACGAAGGTTCCTTGG
ACGTTCGGTGGAGGCACCAAGCTGGAAATCAAACGGACTGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
``` heavy-chain (chimeric version):

CD95-VDJ + human CH1 + hinge + modified CH2 + CD20scFv (VH-VL)

chimeric heavy chain w/o leader-peptide

SEQ ID 23:
```
1             EVQLVETGGG   LVQPKGSLKL   SCAASGFTFN   TNAMNWVRQA   PGKGLEWVAR
51    IRSKSNNYAT  YYAESVKDRF  TISRDDSQSM  LYLQMNNLKA  EDTAMYYCVT
101       DGYYWGQGTT   LTVSSASTKG   PSVFPLAPSS   KSTSGGTAAL   GCLVKDYFPE
151       PVTVSWNSGA   LTSGVHTFPA   VLQSSGLYSL   SSVVTVPSSS   LGTQTYICNV
201       NHKPSNTKVD   KKVEPKSCDK   THTSPPSPAP   PVAGPSVFLF   PPKPKDTLMI
251       SRTPEVTCVV   VGVSHEDPEV   KFNWYVDGVE   VHNAKTKPRE   EQYQSTYRVV
301       SVLTVLHQDW   LNGKEYKCKV   SNKQLPSPIE   KTISKAKGQP   SGQAYLQQSG
351       AELVRPGASV   KMSCKASGYT   FTSYNMHWVK   QTPRQGLEWI   GAIYPGNGDT
401       SYNQKFKGKA   TLTVDKSSST   AYMQLSSLTS   EDSAVYFCAR   VVYYSNSYWY
451       FDVWGTGTTVTVSSGGGGSG   GGGSGGGGSD   IVLSQSPAIL   SASPGEKVTM
501   TCRASSSVSY   MHWYQQKPGS   SPKPWIYAPS   NLASGVPARF   SGSGSGTSYS
551   LTISRVEAED  AATYYCQQWS  FNPPTFGAGT  KLELK**
```

- Amino acids 1-115: anti-CD95 VDJ (mouse)
- amino acids underlined: human CH1, modified hinge and modified CH2 followed by GQP (= first three amino acids from CH3) followed by amino acids SG
- *italic* amino acids 343 - 464 anti-CD20 (VH) GenBank # M17953
- GGGGSGGGGSGGGGS (SEQ ID 24) linker element between Vh and Vl
- bold amino acids 480 - end (585) anti-CD20 (VL) GenBank # M17954

Fig. 2E (continued)

Nucleotide sequence (SEQ ID 25):

```
GAGGTGCAGCTTGTTGAGACTGGTGGAGGATTGGTGCAGCCTAAAGGGTCATTGAAACTC
TCATGTGCAGCCTCTGGATTCACCTTCAATACCAATGCCATGAACTGGGTCCGCCAGGCT
CCAGGAAAGGGTTTGGAATGGGTTGCTCGCATAAGAAGTAAAAGTAATAATTATGCAACA
TACTATGCCGAATCAGTGAAAGACAGGTTCACCATCTCCAGAGATGATTCACAAAGCATG
CTCTATCTGCAAATGAACAACTTGAAAGCTGAGGACACAGCCATGTATTACTGTGTGACT
GATGGTTACTACTGGGGCCAAGGCACCACTCTCACAGTCTCCTCAGGGCAGCCCTCCGGA
CAGGCTTATCTACAGCAGTCTGGGGCTGAGCTGGTGAGGCCTGGGGCCTCAGTGAAGATG
TCCTGCAAGGCTTCTGGCTACACATTTACCAGTTACAATATGCACTGGGTAAAGCAGACA
CCTAGACAGGGCCTGGAATGGATTGGAGCTATTTATCCAGGAAATGGTGATACTTCCTAC
AATCAGAAGTTCAAGGGCAAGGCCACACTGACTGTAGACAAATCCTCCAGCACAGCCTAC
ATGCAGCTCAGCAGCCTGACCTCTGAAGACTCTGCGGTCTATTTCTGTGCAAGAGTGGTG
TACTATAGTAACTCTTACTGGTACTTCGACGTCTGGGGCACAGGGACCACGGTCACCGTC
TCCTCAGGTGGAGGCGGTTCAGGCGGAGGTGGCTCTGGCGGTGGCGGATCGGACATCGTT
CTCTCCCAGTCTCCAGCTATCTTGTCTGCATCTCCAGGGGAGAAGGTCACCATGACTTGC
AGAGCCAGTTCAAGTGTTAGTTACATGCACTGGTACCAGCAGAAGCCAGGATCCTCCCCC
AAACCCTGGATTTATGCCCCATCCAACCTGGCTTCTGGAGTCCCTGCTCGCTTCAGTGGC
AGTGGGTCTGGGACCTCTTACTCTCTCACAATCAGCAGAGTGGAGGCTGAAGATGCTGCC
ACTTATTACTGCCAGCAGTGGAGTTTTAACCCACCCACGTTCGGTGCTGGGACCAAGCTG
GAGCTGAAATGATAA
```

Fig. 2E (continued)

ii) humanised versions light-chain (humanised version):

humanised CD95-VJ / human CL

SEQ ID 26:

```
     DIVMTQSPDSLAVSLGERATISCRASESVEYYGTSLMQWYQQKPGQPPKLLIYVASNVES
   1 ---------+---------+---------+---------+---------+---------+  60

GVPDRFSGSGSGTDFTLTISSLQAEDVAVYFCQQSTKVPWTFGQGTKLEIKRTVAAPSVF
  61 ---------+---------+---------+---------+---------+---------+ 120

IFPPSDEQLKSGTASVVCLLNNFYPREAKVQWKVDNALQSGNSQESVTEQDSKDSTYSLS
 121 ---------+---------+---------+---------+---------+---------+ 180

STLTLSKADYEKHKVYACEVTHQGLSSPVTKSFNRGEC*
 181 ---------+---------+---------+--------- 219
```

Nucleotide sequence (SEQ ID 27):

Nt-sequence of:
humanized CD95-VJ + human kappa LC
underlined: murine Ig kappa LC signal sequence
bold: stop codon

```
ATGGAGACCGACACCCTGCTGCTGTGGGTGCTGCTGCTGTGGGTGCCCGGCTCCACCGGCGACATCGTGATGACCC
AGTCCCCCGACTCCCTGGCCGTGTCCCTGGGCGAGAGGGCCACCATCTCCTGCAGGGCCTCCGAGTCCGTGGAGTA
CTACGGCACCTCCCTGATGCAGTGGTACCAGCAGAAGCCCGGCCAGCCCCCAAGCTGCTGATCTACGTGGCCTCC
AACGTGGAGTCCGGCGTGCCCGACAGGTTCTCCGGCTCCGGCTCCGGCACCGACTTCACCCTGACCATCTCCTCCC
TGCAGGCCGAGGACGTGGCCGTGTACTTCTGCCAGCAGTCCACCAAGGTGCCCTGGACCTTCGGCCAGGGCACCAA
GCTGGAGATCAAGCGTACGGTGGCCGCCCCTCCGTGTTCATCTTCCCCCCCTCCGACGAGCAGCTGAAGTCCGGC
ACCGCCTCCGTGGTGTGCCTGCTGAACAACTTCTACCCCAGGGAGGCCAAGGTGCAGTGGAAGGTGGACAACGCCC
TGCAGTCCGGCAACTCCCAGGAGTCCGTGACCGAGCAGGACTCCAAGGACTCCACCTACTCCCTGTCCTCCACCCT
GACCCTGTCCAAGGCCGACTACGAGAAGCACAAGGTCTACGCCTGCGAGGTGACCCACCAGGGCCTGTCCTCCCCC
GTGACCAAGTCCTTCAACAGGGGCGAGTGCTGA
```

Fig. 2E (continued)

heavy-chain (humanised version):

humanised CD95-VDJ-CH1-H-CH2(attenuated)/ humanised CD20scFv (VH-VL)

SEQ ID 28:

```
            EVQLVESGGGLVKPGGSLRLSCAASGFTFNTNAMNWVRQAPGKGLEWVARIRSKSNNYAT
      1     ---------+---------+---------+---------+---------+---------+    60

YYAESVKDRFTISRDDSKNTLYLQMNSLKTEDTAVYYCVTDGYYWGQGTTLTVSSASTKG
     61     ---------+---------+---------+---------+---------+---------+   120

PSVFPLAPSSKSTSGGTAALGCLVKDYFPEPVTVSWNSGALTSGVHTFPAVLQSSGLYSL
    121     ---------+---------+---------+---------+---------+---------+   180

SSVVTVPSSSLGTQTYICNVNHKPSNTKVDKKVEPKSCDKTHTSPPSPAPPVAGPSVFLF
    181     ---------+---------+---------+---------+---------+---------+   240

PPKPKDTLMISRTPEVTCVVVGVSHEDPEVKFNWYVDGVEVHNAKTKPREEQYQSTYRVV
    241     ---------+---------+---------+---------+---------+---------+   300

SVLTVLHQDWLNGKEYKCKVSNKQLPSPIEKTISKAKGQPSGQVQLVQSGAEVKKPGASV
    301     ---------+---------+---------+---------+---------+---------+   360

KVSCKASGYTFTSYNMHWVRQAPGQGLEWIGAIYPGNGDTSYNQKFKGRVTITRDTSAST
    361     ---------+---------+---------+---------+---------+---------+   420

AYMELSSLRSEDTAVYYCARVVYYSNSYWYFDVWGQGTLVTVSSGGGGSGGGGSGGGGSD
    421     ---------+---------+---------+---------+---------+---------+   480

IQMTQSPSSLSASVGDRVTITCRASSSVSYMHWYQQKPGKAPKPLIYAPSNLASGVPSRF
    481     ---------+---------+---------+---------+---------+---------+   540

SGSGSGTDFTLTISSLQPEDFATYYCQQWSFNPPTFGQGTKLEIK**
    541     ---------+---------+---------+---------+-------   587
```

Fig. 2E (continued)

Nucleotide sequence (SEQ ID 29):

Nt-sequence of:
humanized CD95-VDJ-CH1-H-CH2 (attenuated) - humanized CD20scFv (VH-VL)
underlined: murine Ig kappa LC signal sequence
bold: stop codon <u>ATGGAGACCGACACCCTGCTGCTGTGGGTGCTGCTGCTGTGGGTGCCCGGCTCCACCGGC</u>GAGGTGCAGCTGGTGG
AGTCCGGCGGCGGCCTGGTGAAGCCCGGCGGCTCCCTGAGGCTGTCCTGCGCCGCCTCCGGCTTCACCTTCAACAC
CAACGCCATGAACTGGGTGAGGCAGGCCCCCGGCAAGGGCCTGGAGTGGGTGGCCAGGATCAGGTCCAAGTCCAAC
AACTACGCCACCTACTACGCCGAGTCCGTGAAGGACAGGTTCACCATCTCCAGGGACGACTCCAAGAACACCCTGT
ACCTGCAGATGAACTCCCTGAAGACCGAGGACACCGCCGTGTACTACTGCGTGACCGACGGCTACTACTGGGGCCA
GGGCACCACCCTGACCGTGTCCTCCGCCTCCACCAAGGGCCCCTCCGTGTTCCCCCTGGCCCCCTCCTCCAAGTCC
ACCTCCGGCGGCACCGCCGCCCTGGGCTGCCTGGTGAAGGACTACTTCCCCGAGCCCGTGACCGTGTCCTGGAACT
CCGGCGCCCTGACCTCCGGCGTGCACACCTTCCCCGCCGTGCTGCAGTCCTCCGGCCTGTACTCCCTGTCCTCCGT
GGTGACCGTGCCCTCCTCCTCCCTGGGCACCCAGACCTACATCTGCAACGTGAACCACAAGCCCTCCAACACCAAG
GTGGACAAGAAGGTGGAGCCCAAGTCCTGCGACAAGACCCACACCTCCCCCCCCTCCCCCGCCCCCCCCGTGGCCG
GCCCCTCCGTGTTCCTGTTCCCCCCCAAGCCCAAGGACACCCTGATGATCTCCAGGACCCCCGAGGTGACCTGCGT
GGTGGTGGGCGTGTCCCACGAGGACCCCGAGGTGAAGTTCAACTGGTACGTGGACGGCGTGGAGGTGCACAACGCC
AAGACCAAGCCCAGGGAGGAGCAGTACCAGTCCACCTACAGGGTGGTGTCCGTGCTGACCGTGCTGCACCAGGACT
GGCTGAACGGCAAGGAGTACAAGTGCAAGGTGTCCAACAAGCAGCTGCCCTCCCCCATCGAGAAGACGATATCCAA
GGCCAAGGGCCAGCCCTCCGGCCAGGTGCAGCTGGTGCAGTCCGGCGCCGAGGTGAAGAAGCCCGGCGCCTCCGTG
AAGGTGTCCTGCAAGGCCTCCGGCTACACCTTCACCTCCTACAACATGCACTGGGTCAGGCAGGCCCCCGGCCAGG
GCCTGGAGTGGATCGGCGCCATCTACCCCGGCAACGGCGACACCTCCTACAACCAGAAGTTCAAGGGCAGGGTGAC
CATCACCAGGGACACCTCCGCCTCCACCGCCTACATGGAGCTGTCCTCCCTGAGGTCCGAGGACACCGCCGTGTAC
TACTGCGCCAGGGTGGTGTACTACTCCAACTCCTACTGGTACTTCGACGTGTGGGGCCAGGGCACCCTGGTGACCG
TGTCCTCCGGCGGCGGCGGCTCCGGCGGCGGCGGATCCGGCGGCGGCGGCTCCGACATCCAGATGACCCAGTCCCC
CTCCTCCCTGTCCGCCTCCGTGGGCGACAGGGTGACCATCACCTGCAGGGCCTCCTCCTCCGTGTCCTACATGCAC
TGGTACCAGCAGAAGCCCGGCAAGGCCCCCAAGCCCCTGATCTACGCCCCCTCCAACCTGGCCTCCGGCGTGCCCT
CCAGGTTCTCCGGCTCCGGCTCCGGCACCGACTTCACCCTGACCATCTCCTCCCTGCAGCCCGAGGACTTCGCCAC
CTACTACTGCCAGCAGTGGTCCTTCAACCCCCCCACCTTCGGCCAGGGCACCAAGCTGGAGATCAAGTGA

SEQUENCE LISTING

```
<160> NUMBER OF SEQ ID NOS: 29

<210> SEQ ID NO 1
<211> LENGTH: 112
<212> TYPE: PRT
<213> ORGANISM: artificial
<220> FEATURE:
<223> OTHER INFORMATION: VL Sequence

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Val Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Thr
                85                  90                  95

Lys Val Pro Trp Thr Phe Gly Gly Gly Thr Lys Leu Glu Ile Lys Arg
            100                 105                 110

<210> SEQ ID NO 2
<211> LENGTH: 15
<212> TYPE: PRT
<213> ORGANISM: artificial
<220> FEATURE:
<223> OTHER INFORMATION: CDR Sequence

<400> SEQUENCE: 2

Arg Ala Ser Glu Ser Val Glu Tyr Tyr Gly Thr Ser Leu Met Gln
1               5                   10                  15

<210> SEQ ID NO 3
<211> LENGTH: 7
<212> TYPE: PRT
<213> ORGANISM: artificial
<220> FEATURE:
<223> OTHER INFORMATION: CDR Sequence

<400> SEQUENCE: 3

Val Ala Ser Asn Val Glu Ser
1               5

<210> SEQ ID NO 4
<211> LENGTH: 9
<212> TYPE: PRT
<213> ORGANISM: artificial
```

<220> FEATURE:
<223> OTHER INFORMATION: CDR Sequence

<400> SEQUENCE: 4

Gln Gln Ser Thr Lys Val Pro Trp Thr
1               5

<210> SEQ ID NO 5
<211> LENGTH: 115
<212> TYPE: PRT
<213> ORGANISM: artificial
<220> FEATURE:
<223> OTHER INFORMATION: VH Sequence

<400> SEQUENCE: 5

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Glu
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Ala Glu Asp Thr Ala Met Tyr
                85                  90                  95

Tyr Cys Val Thr Asp Gly Tyr Tyr Trp Gly Gln Gly Thr Thr Leu Thr
            100                 105                 110

Val Ser Ser
        115

<210> SEQ ID NO 6
<211> LENGTH: 5
<212> TYPE: PRT
<213> ORGANISM: artificial
<220> FEATURE:
<223> OTHER INFORMATION: CDR Sequence

<400> SEQUENCE: 6

Thr Asn Ala Met Asn
1               5

<210> SEQ ID NO 7
<211> LENGTH: 19
<212> TYPE: PRT
<213> ORGANISM: artificial
<220> FEATURE:
<223> OTHER INFORMATION: CDR Sequence

<400> SEQUENCE: 7

Arg Ile Arg Ser Lys Ser Asn Asn Tyr Ala Thr Tyr Tyr Ala Glu Ser
1               5                   10                  15

Val Lys Asp

<210> SEQ ID NO 8
<211> LENGTH: 4
<212> TYPE: PRT
<213> ORGANISM: artificial
<220> FEATURE:
<223> OTHER INFORMATION: CDR Sequence

<400> SEQUENCE: 8

Asp Gly Tyr Tyr
1

<210> SEQ ID NO 9
<211> LENGTH: 111
<212> TYPE: PRT
<213> ORGANISM: artificial
<220> FEATURE:
<223> OTHER INFORMATION: VL Sequence

<400> SEQUENCE: 9

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Val Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Ser Thr
                85                  90                  95

Lys Val Pro Trp Thr Phe Gly Gln Gly Thr Lys Leu Glu Ile Lys
            100                 105                 110

<210> SEQ ID NO 10
<211> LENGTH: 115
<212> TYPE: PRT
<213> ORGANISM: artificial
<220> FEATURE:
<223> OTHER INFORMATION: VH Sequence

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Glu
    50                  55                  60

Ser Val Lys Asp Arg Phe Thr Ile Ser Arg Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Thr Asp Gly Tyr Tyr Trp Gly Gln Gly Thr Thr Leu Thr
            100                 105                 110

Val Ser Ser
        115

<210> SEQ ID NO 11
<211> LENGTH: 106
<212> TYPE: PRT
<213> ORGANISM: artificial
<220> FEATURE:
<223> OTHER INFORMATION: VL Sequence

<400> SEQUENCE: 11

-continued

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
            35                  40                  45

Ala Pro Ser Asn Leu Ala Ser Gly Val Pro Ala Arg Phe Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys
            100                 105

<210> SEQ ID NO 12
<211> LENGTH: 9
<212> TYPE: PRT
<213> ORGANISM: artificial
<220> FEATURE:
<223> OTHER INFORMATION: CDR Sequence

<400> SEQUENCE: 12

Arg Ala Ser Ser Ser Val Ser Tyr Met
1               5

<210> SEQ ID NO 13
<211> LENGTH: 7
<212> TYPE: PRT
<213> ORGANISM: artificial
<220> FEATURE:
<223> OTHER INFORMATION: CDR Sequence

<400> SEQUENCE: 13

Ala Pro Ser Asn Leu Ala Ser
1               5

<210> SEQ ID NO 14
<211> LENGTH: 9
<212> TYPE: PRT
<213> ORGANISM: artificial
<220> FEATURE:
<223> OTHER INFORMATION: CDR Sequence

<400> SEQUENCE: 14

Gln Gln Trp Ser Phe Asn Pro Pro Thr
1               5

<210> SEQ ID NO 15
<211> LENGTH: 122
<212> TYPE: PRT
<213> ORGANISM: artificial
<220> FEATURE:
<223> OTHER INFORMATION: VH Sequence

<400> SEQUENCE: 15

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
            35                  40                  45

```
Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ser
        115                 120

<210> SEQ ID NO 16
<211> LENGTH: 5
<212> TYPE: PRT
<213> ORGANISM: artificial
<220> FEATURE:
<223> OTHER INFORMATION: CDR Sequence

<400> SEQUENCE: 16

Ser Tyr Asn Met His
1               5

<210> SEQ ID NO 17
<211> LENGTH: 17
<212> TYPE: PRT
<213> ORGANISM: artificial
<220> FEATURE:
<223> OTHER INFORMATION: CDR Sequence

<400> SEQUENCE: 17

Ala Ile Tyr Pro Gly Asn Gly Asp Thr Ser Tyr Asn Gln Lys Phe Lys
1               5                   10                  15

Gly

<210> SEQ ID NO 18
<211> LENGTH: 13
<212> TYPE: PRT
<213> ORGANISM: artificial
<220> FEATURE:
<223> OTHER INFORMATION: CDR Sequence

<400> SEQUENCE: 18

Val Val Tyr Tyr Ser Asn Ser Tyr Trp Tyr Phe Asp Val
1               5                   10

<210> SEQ ID NO 19
<211> LENGTH: 106
<212> TYPE: PRT
<213> ORGANISM: artificial
<220> FEATURE:
<223> OTHER INFORMATION: VL Sequence

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
                20                  25                  30

His Trp Tyr Gln Gln Lys Pro Gly Lys Ala Pro Lys Pro Leu Ile Tyr
            35                  40                  45

Ala Pro Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
```

```
                65                  70                  75                  80
Asp Phe Ala Thr Tyr Tyr Cys Gln Gln Trp Ser Phe Asn Pro Pro Thr
                        85                  90                  95

Phe Gly Gln Gly Thr Lys Leu Glu Ile Lys
                100                 105

<210> SEQ ID NO 20
<211> LENGTH: 122
<212> TYPE: PRT
<213> ORGANISM: artificial
<220> FEATURE:
<223> OTHER INFORMATION: VH Sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Val Tyr Tyr Ser Asn Ser Tyr Trp Tyr Phe Asp Val Trp
                100                 105                 110

Gly Gln Gly Thr Leu Val Thr Val Ser Ser
            115                 120

<210> SEQ ID NO 21
<211> LENGTH: 218
<212> TYPE: PRT
<213> ORGANISM: artificial
<220> FEATURE:
<223> OTHER INFORMATION: LC Sequence

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
                20                  25                  30

Gly Thr Ser Leu Met Gln Trp Tyr Gln Gln Lys Pro Gly Gln Pro Pro
            35                  40                  45

Lys Leu Leu Ile Tyr Val Ala Ser Asn Val Glu Ser Gly Val Pro Ala
        50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Thr
                85                  90                  95

Lys Val Pro Trp Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 22
<211> LENGTH: 657
<212> TYPE: DNA
<213> ORGANISM: artificial
<220> FEATURE:
<223> OTHER INFORMATION: LC Sequence

<400> SEQUENCE: 22

```
gacattgtgc tcacccaatc tccagcttct ttggctgtgt ctctagggca gagagccacc      60
atctcctgca gagccagtga aagtgttgaa tattatggca aagtttaat gcaatggtac     120
caacagaagc caggacagcc acccaaactc ctcatctatg ttgcatccaa cgtagaatct     180
ggggtccctg ccaggtttag tggcagtggg tctgggacag acttcagcct caacatccac     240
cctgtggagg aggatgatat tgcaatgtat ttctgtcagc aaagtacgaa ggttccttgg     300
acgttcggtg gaggcaccaa gctggaaatc aaacggactg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc     600
acccatcagg gcctgagctc gcccgtcaca aagagcttca cagggagag tgttag          657
```

<210> SEQ ID NO 23
<211> LENGTH: 585
<212> TYPE: PRT
<213> ORGANISM: artificial
<220> FEATURE:
<223> OTHER INFORMATION: HC Sequence

<400> SEQUENCE: 23

```
Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Glu
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Ala Glu Asp Thr Ala Met Tyr
                85                  90                  95

Tyr Cys Val Thr Asp Gly Tyr Tyr Trp Gly Gln Gly Thr Thr Leu Thr
            100                 105                 110

Val Ser Ser Ala Ser Thr Lys Gly Pro Ser Val Phe Pro Leu Ala Pro
```

-continued

```
            115                 120                 125
Ser Ser Lys Ser Thr Ser Gly Gly Thr Ala Ala Leu Gly Cys Leu Val
            130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
Val Asp Lys Lys Val Glu Pro Lys Ser Cys Asp Lys Thr His Thr Ser
210                 215                 220
Pro Pro Ser Pro Ala Pro Pro Val Ala Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Gly Val Ser His Glu Asp Pro Glu Val Lys Phe
                260                 265                 270
Asn Trp Tyr Val Asp Gly Val Glu Val His Asn Ala Lys Thr Lys Pro
                275                 280                 285
Arg Glu Glu Gln Tyr Gln Ser Thr Tyr Arg Val Val Ser Val Leu Thr
                290                 295                 300
Val Leu His Gln Asp Trp Leu Asn Gly Lys Glu Tyr Lys Cys Lys Val
305                 310                 315                 320
Ser Asn Lys Gln Leu Pro Ser Pro Ile Glu Lys Thr Ile Ser Lys Ala
                325                 330                 335
Lys Gly Gln Pro Ser Gly Gln Ala Tyr Leu Gln Gln Ser Gly Ala Glu
                340                 345                 350
Leu Val Arg Pro Gly Ala Ser Val Lys Met Ser Cys Lys Ala Ser Gly
                355                 360                 365
Tyr Thr Phe Thr Ser Tyr Asn Met His Trp Val Lys Gln Thr Pro Arg
                370                 375                 380
Gln Gly Leu Glu Trp Ile Gly Ala Ile Tyr Pro Gly Asn Gly Asp Thr
385                 390                 395                 400
Ser Tyr Asn Gln Lys Phe Lys Gly Lys Ala Thr Leu Thr Val Asp Lys
                405                 410                 415
Ser Ser Ser Thr Ala Tyr Met Gln Leu Ser Ser Leu Thr Ser Glu Asp
                420                 425                 430
Ser Ala Val Tyr Phe Cys Ala Arg Val Val Tyr Tyr Ser Asn Ser Tyr
                435                 440                 445
Trp Tyr Phe Asp Val Trp Gly Thr Gly Thr Thr Val Thr Val Ser Ser
                450                 455                 460
Gly Gly Gly Gly Ser Gly Gly Gly Ser Gly Gly Gly Gly Ser Asp
465                 470                 475                 480
Ile Val Leu Ser Gln Ser Pro Ala Ile Leu Ser Ala Ser Pro Gly Glu
                485                 490                 495
Lys Val Thr Met Thr Cys Arg Ala Ser Ser Ser Val Ser Tyr Met His
                500                 505                 510
Trp Tyr Gln Gln Lys Pro Gly Ser Ser Pro Lys Pro Trp Ile Tyr Ala
                515                 520                 525
Pro Ser Asn Leu Ala Ser Gly Val Pro Ala Arg Phe Ser Gly Ser Gly
                530                 535                 540
```

Ser Gly Thr Ser Tyr Ser Leu Thr Ile Ser Arg Val Glu Ala Glu Asp
545                 550                 555                 560

Ala Ala Thr Tyr Tyr Cys Gln Gln Trp Ser Phe Asn Pro Pro Thr Phe
            565                 570                 575

Gly Ala Gly Thr Lys Leu Glu Leu Lys
        580                 585

<210> SEQ ID NO 24
<211> LENGTH: 15
<212> TYPE: PRT
<213> ORGANISM: artificial
<220> FEATURE:
<223> OTHER INFORMATION: Linker

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 1095
<212> TYPE: DNA
<213> ORGANISM: artificial
<220> FEATURE:
<223> OTHER INFORMATION: HC Sequence

<400> SEQUENCE: 25
gaggtgcagc ttgttgagac tggtggagga ttggtgcagc ctaaagggtc attgaaactc        60
tcatgtgcag cctctggatt caccttcaat accaatgcca tgaactgggt ccgccaggct       120
ccaggaaagg gtttggaatg ggttgctcgc ataagaagta aaagtaataa ttatgcaaca       180
tactatgccg aatcagtgaa agacaggttc accatctcca gagatgattc acaaagcatg       240
ctctatctgc aaatgaacaa cttgaaagct gaggacacag ccatgtatta ctgtgtgact       300
gatggttact actggggcca aggcaccact ctcacagtct cctcagggca gccctccgga       360
caggcttatc tacagcagtc tggggctgag ctggtgaggc ctggggcctc agtgaagatg       420
tcctgcaagg cttctggcta cacatttacc agttacaata tgcactgggt aaagcagaca       480
cctagacagg gcctggaatg gattggagct atttatccag gaaatggtga tacttcctac       540
aatcagaagt tcaagggcaa ggccacactg actgtagaca atcctccag cacagcctac       600 atgcagctca gcagcctgac ctctgaagac tctgcggtct atttctgtgc aagagtggtg       660
tactatagta actcttactg gtacttcgac gtctggggca gggaccac ggtcaccgtc        720 tcctcaggtg gaggcggttc aggcggaggt ggctctggcg gtggcggatc ggacatcgtt       780
ctctcccagt ctccagctat cttgtctgca tctccagggg agaaggtcac catgacttgc       840
agagccagtt caagtgttag ttacatgcac tggtaccagc agaagccagg atcctccccc       900
aaaccctgga tttatgcccc atccaacctg gcttctggag tccctgctcg cttcagtggc       960
agtgggtctg ggacctctta ctctctcaca atcagcagag tggaggctga agatgctgcc      1020
acttattact gccagcagtg gagttttaac ccacccacgt tcggtgctgg gaccaagctg      1080
gagctgaaat gataa                                                       1095

<210> SEQ ID NO 26
<211> LENGTH: 218
<212> TYPE: PRT
<213> ORGANISM: artificial
<220> FEATURE:
<223> OTHER INFORMATION: LC Sequence

<400> SEQUENCE: 26

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Val Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Ser Thr
                85                  90                  95

Lys Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 27
<211> LENGTH: 717
<212> TYPE: DNA
<213> ORGANISM: artificial
<220> FEATURE:
<223> OTHER INFORMATION: LC Sequence

<400> SEQUENCE: 27
atggagaccg acaccctgct gctgtgggtg ctgctgctgt gggtgcccgg ctccaccggc      60
gacatcgtga tgacccagtc ccccgactcc ctggccgtgt ccctgggcga gagggccacc     120
atctcctgca gggcctccga gtccgtggag tactacggca cctccctgat gcagtggtac     180
cagcagaagc ccggccagcc ccccaagctg ctgatctacg tggcctccaa cgtggagtcc     240
ggcgtgcccg acaggttctc cggctccggc tccggcaccg acttcaccct gaccatctcc     300
tccctgcagg ccgaggacgt ggccgtgtac ttctgccagc agtccaccaa ggtgccctgg     360
accttcggcc agggcaccaa gctggagatc aagcgtacgg tggccgcccc ctccgtgttc     420
atcttccccc cctccgacga gcagctgaag tccggcaccg cctccgtggt gtgcctgctg     480
aacaacttct accccaggga ggccaaggtg cagtggaagg tggacaacgc cctgcagtcc     540
ggcaactccc aggagtccgt gaccgagcag gactccaagg actccaccta ctccctgtcc     600
tccaccctga ccctgtccaa ggccgactac gagaagcaca aggtctacgc ctgcgaggtg     660
acccaccagg gcctgtcctc ccccgtgacc aagtccttca caggggcga gtgctga       717

<210> SEQ ID NO 28
<211> LENGTH: 585
<212> TYPE: PRT
<213> ORGANISM: artificial
<220> FEATURE:
<223> OTHER INFORMATION: HC Sequence

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Glu
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Thr Asp Gly Tyr Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ser
    210                 215                 220

Pro Pro Ser Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Gly Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Gln Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gln Leu Pro Ser Pro Ile Glu Lys Thr Ile Ser Lys Ala
                325                 330                 335

Lys Gly Gln Pro Ser Gly Gln Val Gln Leu Val Gln Ser Gly Ala Glu
            340                 345                 350

Val Lys Lys Pro Gly Ala Ser Val Lys Val Ser Cys Lys Ala Ser Gly
        355                 360                 365

Tyr Thr Phe Thr Ser Tyr Asn Met His Trp Val Arg Gln Ala Pro Gly

Gln Gly Leu Glu Trp Ile Gly Ala Ile Tyr Pro Gly Asn Gly Asp Thr
385                 390                 395                 400

Ser Tyr Asn Gln Lys Phe Lys Gly Arg Val Thr Ile Thr Arg Asp Thr
                405                 410                 415

Ser Ala Ser Thr Ala Tyr Met Glu Leu Ser Ser Leu Arg Ser Glu Asp
            420                 425                 430

Thr Ala Val Tyr Tyr Cys Ala Arg Val Val Tyr Tyr Ser Asn Ser Tyr
        435                 440                 445

Trp Tyr Phe Asp Val Trp Gly Gln Gly Thr Leu Val Thr Val Ser Ser
    450                 455                 460

Gly Gly Gly Gly Ser Gly Gly Gly Ser Gly Gly Gly Gly Ser Asp
465                 470                 475                 480

Ile Gln Met Thr Gln Ser Pro Ser Ser Leu Ser Ala Ser Val Gly Asp
                485                 490                 495

Arg Val Thr Ile Thr Cys Arg Ala Ser Ser Ser Val Ser Tyr Met His
            500                 505                 510

Trp Tyr Gln Gln Lys Pro Gly Lys Ala Pro Lys Pro Leu Ile Tyr Ala
        515                 520                 525

Pro Ser Asn Leu Ala Ser Gly Val Pro Ser Arg Phe Ser Gly Ser Gly
    530                 535                 540

Ser Gly Thr Asp Phe Thr Leu Thr Ile Ser Ser Leu Gln Pro Glu Asp
545                 550                 555                 560

Phe Ala Thr Tyr Tyr Cys Gln Gln Trp Ser Phe Asn Pro Pro Thr Phe
                565                 570                 575

Gly Gln Gly Thr Lys Leu Glu Ile Lys
            580                 585

<210> SEQ ID NO 29
<211> LENGTH: 1818
<212> TYPE: DNA
<213> ORGANISM: artificial
<220> FEATURE:
<223> OTHER INFORMATION: HC Sequence

<400> SEQUENCE: 29
atggagaccg acaccctgct gctgtgggtg ctgctgctgt gggtgcccgg ctccaccggc        60
gaggtgcagc tggtggagtc cggcggcggc ctggtgaagc ccggcggctc cctgaggctg       120
tcctgcgccg cctccggctt caccttcaac accaacgcca tgaactgggt gaggcaggcc       180
cccggcaagg gcctggagtg ggtggccagg atcaggtcca gtccaacaa ctacgccacc        240 tactacgccg agtccgtgaa ggacaggttc accatctcca gggacgactc caagaacacc       300
ctgtacctgc agatgaactc cctgaagacc gaggacaccg ccgtgtacta ctgcgtgacc       360
gacggctact actggggcca gggcaccacc ctgaccgtgt cctccgcctc caccaagggc       420
ccctccgtgt tccccctggc ccctcctcc aagtccacct ccggcggcac cgccgccctg        480
ggctgcctgg tgaaggacta cttccccgag cccgtgaccg tgtcctggaa ctccggcgcc       540
ctgacctccg gcgtgcacac cttccccgcc gtgctgcagt cctccggcct gtactccctg       600
tcctccgtgg tgaccgtgcc ctcctcctcc tgggcaccc agacctacat ctgcaacgtg        660
aaccacaagc cctccaacac caaggtggac aagaaggtgg agcccaagtc ctgcgacaag       720
acccacacct cccccccctc cccgccccc ccgtggccg ccctccgt gttcctgttc           780 ccccccaagc ccaaggacac cctgatgatc tccaggaccc ccgaggtgac ctgcgtggtg       840

```
gtgggcgtgt cccacgagga ccccgaggtg aagttcaact ggtacgtgga cggcgtggag      900
gtgcacaacg ccaagaccaa gcccaggggag gagcagtacc agtccaccta cagggtggtg      960
tccgtgctga ccgtgctgca ccaggactgg ctgaacggca aggagtacaa gtgcaaggtg     1020
tccaacaagc agctgccctc ccccatcgag aagacgatat ccaaggccaa gggccagccc     1080
tccggccagg tgcagctggt gcagtccggc gccgaggtga agaagcccgg cgcctccgtg     1140
aaggtgtcct gcaaggcctc cggctacacc ttcacctcct acaacatgca ctgggtcagg     1200
caggcccccg gccagggcct ggagtggatc ggcgccatct accccggcaa cggcgacacc     1260
tcctacaacc agaagttcaa gggcagggtg accatcacca gggacacctc cgcctccacc     1320
gcctacatgg agctgtcctc cctgaggtcc gaggacaccg ccgtgtacta ctgcgccagg     1380
gtggtgtact actccaactc ctactggtac ttcgacgtgt ggggccaggg caccctggtg     1440
accgtgtcct ccggcggcgg cggctccggc ggcggcggat ccggcggcgg cggctccgac     1500
atccagatga cccagtcccc ctcctccctg tccgcctccg tgggcgacag ggtgaccatc     1560
acctgcaggg cctcctcctc cgtgtcctac atgcactggt accagcagaa gcccggcaag     1620
gcccccaagc ccctgatcta cgccccctcc aacctggcct ccggcgtgcc ctccaggttc     1680
tccggctccg gctccggcac cgacttcacc ctgaccatct cctccctgca gcccgaggac     1740
ttcgccacct actactgcca gcagtggtcc ttcaaccccc ccaccttcgg ccagggcacc     1800
aagctggaga tcaagtga                                                  1818
```

RECOMBINANT BISPECIFIC ANTIBODY BINDING TO CD20 AND CD95

The invention refers to a new bispecific antibody format binding to CD20 and CD95.

BACKGROUND

CD95/Fas/Apo-1 is a cell surface receptor capable of inducing apoptotic death of human cells. Similar to the physiologic ligand of this receptor, CD95L, agonistic anti-CD95 antibodies may induce apoptosis if binding to CD95 occurs in a multimeric format, e.g., as pentameric IgM or self-aggregating IgG3. Alternatively, anti-CD95 antibodies may be cross-linked by Fc receptors on neighbouring cells or by secondary antibodies to achieve agonistic activity.

Because many tumor cells express CD95, the use of agonistic anti-CD95 antibodies for tumor therapy has been vigorously pursued after initial characterization of prototypic CD95 antibodies. However, it soon became obvious that, at least in its most simple form of applying agonistic anti-CD95 antibodies or recombinant CD95L to patients, this approach fails because many normal cell types express functional CD95 and may be killed by agonistic antibodies.

CD20 is a marker of B-cells involved in many lymphoma and autoimmune diseases, e.g. multiple sclerosis (MS), rheumatoid arthritis (RA) and systemic lupus erythematosus (SLE).

Antibodies directed against the B-cell associated CD20 surface antigen can target normal as well as malignant B cells. They are successfully used for the treatment of B-cell derived leukaemia and lymphoma and antibody mediated autoimmune disease, respectively. Rituximab (trade names Rituxan and MabThera) is a chimeric monoclonal antibody against the protein CD20. Rituximab destroys B cells, and is therefore used to treat diseases which are characterized by excessive numbers of B cells, overactive B cells, or dysfunctional B cells. This includes many lymphomas, leukaemias, transplant rejection, and some autoimmune disorders.

However, rituximab kills CD20-positive cells non-specifically, and was shown to be clinically effective in MS but is compromised by side effects (e.g. Progressive Multifocal Leukoencephalopathy, PML).

It was previously shown that bispecific F(ab')$_2$ fragments (bs-F(ab')$_2$) with specificity for CD95 and different target antigens on lymphoma cells, such as CD20 and CD40, induce the apoptosis of cells positive for CD95 and the respective target antigen. Lymphoma cells expressing CD95 but no target antigen were not killed (Jung et al. Cancer Research 61, 1846-1848 (2001)).

Herrmann et al. (Cancer Research 68 (4): 1221-7 (2008) assessed the influence of the antibody format and nature of the target antigen on selective CD95 mediated apoptosis in tumor cells.

US2003/0232049A1 describes a multispecific reagent for selectively stimulating cell surface receptors. Bi-specific antibodies consisting of antigen-binding antibody fragments with a first binding site for a cell surface receptor, such as a death receptor, e.g. CD95, and a second binding site for a target antigen of the same cell, such as CD20 or CD40, are described to kill cancer cells.

SUMMARY OF THE INVENTION

It is the objective of the invention to provide for a bispecific antibody format directed against CD20 and CD95 with improved biological activity.

The object is solved by the subject matter as claimed.

According to the invention there is provided a bispecific antibody format, which comprises or consist of
a) a Fab fragment comprising a first binding site for a first antigen;
b) an scFv fragment comprising a second binding site for a second antigen;
c) optionally linker sequence(s); and
d) a CH2 domain, wherein the Fab fragment and the scFv fragment are linked via the CH2 domain, wherein
the first antigen is CD95 and the second antigen is CD20; or
the first antigen is CD20 and the second antigen is CD95.

Specifically, the antibody format comprises a structure as depicted in FIG. 1. It is termed for example, NA-C20 or Novotarg.

According to a specific embodiment, the format is a construct comprising or consisting of
a) a Fab fragment consisting of a VL/VH domain pair and a CL/CH1 domain pair, which Fab fragment comprises the first binding site;
b) an scFv consisting of VH/VL domains linked to each other;
c) optionally linker sequence(s); and
d) a CH2 domain linking the CH1 domain of the Fab fragment of a) to the VH domain of the scFv of b), wherein
the first antigen is CD95 and the second antigen is CD20; or
the first antigen is CD20 and the second antigen is CD95.

The structure is based on specific antibody domains with or without linker sequences.

The antibody format of the invention is preferably a recombinant antibody format, produced by a recombinant hot cell that comprises heterologous sequences to express said antibody format.

Preferably, the antibody format of the invention is a monoclonal antibody format, which may comprise native amino acid sequences or comprise one or more mutations of the amino acid sequence, the tertiary structure and optionally the glycosylation, e.g. to improve the specificity, the affinity and/or avidity of binding to a target, or to improve the stability of the format, or to increase the producibility of the recombinant molecule.

Specifically, the antibody domains are of mammalian origin, such as rodent, e.g. murine, or human origin, or chimeric or humanized antibody domains of mammalian origin other than human, such as humanized murine or camelid antibody domains.

According to a specific aspect, the binding site that binds CD20 comprises six complementarity determining regions of antibody variable domains (CDR1 to CDR6), wherein
A)
i) CDR1 comprises the amino acid sequence RASSSVSYM (SEQ ID 12);
ii) CDR2 comprises the amino acid sequence APSNLAS (SEQ ID 13);
iii) CDR3 comprises the amino acid sequence QQWSFNPPT (SEQ ID 14);
iv) CDR4 comprises the amino acid sequence SYNMH (SEQ ID 16);
v) CDR5 comprises the amino acid sequence AIYPGNGDTSYNQKFKG (SEQ ID 17); and
vi) CDR6 comprises the amino acid sequence VVYYSNSYWYFDV (SEQ ID 18);
or
B) a functionally active variant thereof, wherein at least one of i) CDR1 comprises an amino acid sequence that has at least 70% sequence identity with the amino acid sequence RASSSVSYM (SEQ ID 12), or at least 80% or at least 90%;

ii) CDR2 comprises an amino acid sequence that has at least 70% sequence identity with the amino acid sequence APSNLAS (SEQ ID 13), or at least 80% or at least 90%;

iii) CDR3 comprises an amino acid sequence that has at least 70% sequence identity with the amino acid sequence QQWSFNPPT (SEQ ID 14), or at least 80% or at least 90%;

iv) CDR4 comprises an amino acid sequence that has at least 70% sequence identity with the amino acid sequence SYNMH (SEQ ID 16), or at least 80% or at least 90%;

v) CDR5 comprises an amino acid sequence that has at least 70% sequence identity with the amino acid sequence AIYPGNGDTSYNQKFKG (SEQ ID 17), or at least 80% or at least 90%; and/or vi) CDR6 comprises an amino acid sequence that has at least 70% sequence identity with the amino acid sequence VVYYSNSYWYFDV (SEQ ID 18), or at least 80% or at least 90%.

The invention specifically contemplates the use of any antibody format comprising an CD20 binding site derived from the sequences A i) to vi) above, e.g. the CDR1, CDR2 and CDR3 sequences of the light chain variable region and/or the CDR4, CDR5 and CDR6 sequences of the heavy chain variable region, including constructs comprising single variable domains comprising either of the combination of the CDR1, CDR2 and CDR3 sequences, or the combination of the CDR4, CDR5 and CDR6 sequences, or pairs of such single variable domains, e.g. VH, VHH or VH/VL domain pairs.

Specific embodiments refer to the antibody format comprising at least one of the CDR sequences of A, preferably at least two or at least three, and at least one of the CDR sequences of B.

Further specific embodiments refer to the antibody format comprising at least one of the CDR sequences of B, preferably at least two or at least three, and at least one of the CDR sequences of A.

Specific embodiments refer to the use of a light chain variable region comprising the CDR1 sequence of A i), the CDR2 of sequence of A ii) and the CDR3 sequence of A iii), and a heavy chain variable region comprising the CDR4 sequence of A iv) or B iv), the CDR5 sequence of A v) or B v) and the CDR6 sequence of A vi) or B vi), wherein at least one of the CDR4, CDR5 and CDR6 sequences comprises a functionally active variant of B.

Further specific embodiments refer to the use of a heavy chain variable region comprising the CDR4 sequence of A iv), the CDR5 of sequence of A v) and the CDR6 sequence of A vi), and a light chain variable region comprising the CDR1 sequence of A i) or B i), the CDR2 sequence of A ii) or B ii) and the CDR3 sequence of A iii) or B iii), wherein at least one of the CDR1, CDR2 and CDR3 sequences comprises a functionally active variant of B.

A variant of B optionally comprise the specific CDR sequence as listed, which contains one, two or three point mutations, e.g. by insertion, deletion, substitution or chemical derivatization of an amino acid residue.

Variants of a CD20 binder are considered functionally active variants, if binding to CD20, specifically human CD20, in particular with a high affinity, e.g. with a $Kd<10^{-8}M$.

According to a specific embodiment, the bispecific antibody format comprises a VL domain comprising or consisting of the amino acid sequence of SEQ ID 11 and/or a VH domain comprising or consisting of the amino acid sequence of SEQ ID 15, or functionally active variants thereof.

Specifically, the variant is a humanized variant comprising a VL domain comprising or consisting of the amino acid sequence of SEQ ID 19 and/or a VH domain comprising or consisting of the amino acid sequence of SEQ ID 20, or a functionally active variant thereof.

According to a specific aspect, the binding site that binds CD95 comprises six complementarity determining regions of variable antibody domains (CDR1 to CDR6), wherein A)
i) CDR1 comprises the amino acid sequence RASESVEYYGTSLMQ (SEQ ID 2);

ii) CDR2 comprises the amino acid sequence VASNVES (SEQ ID 3);

iii) CDR3 comprises the amino acid sequence QQSTKVPWT (SEQ ID 4);

iv) CDR4 comprises the amino acid sequence TNAMN (SEQ ID 6);

v) CDR5 comprises the amino acid sequence RIRSKSNNYATYYAESVKD (SEQ ID 7); and vi) CDR6 comprises the amino acid sequence DGYY (SEQ ID 8);

or

B) a functionally active variant thereof, wherein at least one of i) CDR1 comprises an amino acid sequence that has at least 70% sequence identity with the amino acid sequence RASESVEYYGTSLMQ (SEQ ID 2), or at least 80% or at least 90%;

ii) CDR2 comprises an amino acid sequence that has at least 70% sequence identity with the amino acid sequence VASNVES (SEQ ID 3), or at least 80% or at least 90%;

iii) CDR3 comprises an amino acid sequence that has at least 70% sequence identity with the amino acid sequence QQSTKVPWT (SEQ ID 4), or at least 80% or at least 90%;

iv) CDR4 comprises an amino acid sequence that has at least 70% sequence identity with the amino acid sequence TNAMN (SEQ ID 6), or at least 80% or at least 90%;

v) CDR5 comprises an amino acid sequence that has at least 70% sequence identity with the amino acid sequence RIRSKSNNYATYYAESVKD (SEQ ID 7), or at least 80% or at least 90%; and/or vi) CDR6 comprises an amino acid sequence that has at least 70% sequence identity with the amino acid sequence DGYY (SEQ ID 8), or at least 80% or at least 90%.

The invention specifically contemplates the use of any antibody format comprising an CD95 binding site derived from the sequences A i) to vi) above, e.g. the CDR1, CDR2 and CDR3 sequences of the light chain variable region and/or the CDR4, CDR5 and CDR6 sequences of the heavy chain variable region, including constructs comprising single variable domains comprising either of the combination of the CDR1, CDR2 and CDR3 sequences, or the combination of the CDR4, CDR5 and CDR6 sequences, or pairs of such single variable domains, e.g. VH, VHH or VH/VL domain pairs.

Specific embodiments refer to the antibody format comprising at least one of the CDR sequences of A, preferably at least two or at least three, and at least one of the CDR sequences of B.

Further specific embodiments refer to the antibody format comprising at least one of the CDR sequences of B, preferably at least two or at least three, and at least one of the CDR sequences of A.

Specific embodiments refer to the use of a light chain variable region comprising the CDR1 sequence of A i), the CDR2 of sequence of A ii) and the CDR3 sequence of A iii), and a heavy chain variable region comprising the CDR4 sequence of A iv) or B iv), the CDR5 sequence of A v) or B v) and the CDR6 sequence of A vi) or B vi), wherein at least one of the CDR4, CDR5 and CDR6 sequences comprises a functionally active variant of B.

Further specific embodiments refer to the use of a heavy chain variable region comprising the CDR4 sequence of A iv), the CDR5 of sequence of A v) and the CDR6 sequence of A vi), and a light chain variable region comprising the CDR1 sequence of A i) or B i), the CDR2 sequence of A ii) or B ii) and the CDR3 sequence of A iii) or B iii), wherein at least one of the CDR1, CDR2 and CDR3 sequences comprises a functionally active variant of B.

A variant of B optionally comprise the specific CDR sequence as listed, which contains one, two or three point mutations, e.g. by insertion, deletion, substitution or chemical derivatization of an amino acid residue.

Variants of a CD95 binder are considered functionally active variants, if binding to CD95, specifically human CD95, in particular with a high affinity, e.g. with a Kd<$10^{-8}$M.

According to a specific embodiment, the bispecific antibody format comprises a VL domain comprising or consisting of the amino acid sequence of SEQ ID 1 and/or a VH domain comprising or consisting of the amino acid sequence of SEQ ID 5, or functionally active variants thereof.

Specifically, the variant is a humanized variant comprising a VL domain comprising or consisting of the amino acid sequence of SEQ ID 9 and/or a VH domain comprising or consisting of the amino acid sequence of SEQ ID 10, or a functionally active variant thereof.

According to another specific embodiment, the bispecific antibody format comprises or consists of a light chain sequence of SEQ ID 21 and a heavy chain sequence of SEQ ID 23, or functionally active variants thereof.

Specifically, the variant is a humanized variant comprising a VL domain comprising or consisting of the amino acid sequence of SEQ ID 26 and/or a VH domain comprising or consisting of the amino acid sequence of SEQ ID 28, or a functionally active variant thereof.

The bispecific antibody format according to the invention specifically comprises murine, chimeric, humanized and/or human sequences.

It is preferred that the bispecific antibody format according to the invention binds CD20 with a Kd<$10^{-8}$ M and/or which binds CD95 with a Kd<$10^{-8}$ M.

An exemplary construct is a recombinant bispecific Fab-single chain (bsFabXsc) with CD20XCD95-specificity schematically described in FIG. 1. It is termed for example, NA-C20 or Novotarg.

Specifically, the format may be derived from an antibody of the IgG class, in particular, any of the IgG1, IgG2 or IgG4 subclasses, specifically comprising antibody domains or sequences derived from a human IgG antibody.

Specifically the format may be derived from a human IgG antibody.

According to another specific aspect, the antibody format is provided for medical use, preferably for use in the treatment or prevention of a B-cell disorder.

According to a specific aspect, the antibody format of the invention is provided for medical use to treat a disease condition associated with an undesired level or up-regulation of B-cells, e.g. excessive or malignant B-cells, or an immune disorder caused by an aberrant, excessive or undesired immune response. Exemplary disease conditions are auto-immune disease or cancer, including leukemia or lymphoma.

According to the invention there is further provided a method for the treatment or prevention of a B-cell disorder comprising administering a therapeutically effective amount of bispecific antibody format to a subject in need thereof.

According to another aspect of the invention, a method is provided for treating B-cells, comprising contacting said cells with a composition comprising the bispecific antibody format of the invention. Such treatment method may be in vivo or ex vivo.

Specifically, the death receptor CD95 and the cell surface antigen CD20 expressed by said cells are targeted by the bispecific antibody format, thereby casing apoptosis and/or inhibition of the cells.

Specifically, the bispecific antibody format of the invention is administered to a subject in need thereof in a therapeutically effective amount, preferably provided in a formulation for parenteral use, e.g. intravenous or subcutaneous formulation, in particular in a pharmaceutical preparation which comprises the antibody format and optionally a pharmaceutically acceptable carrier or excipient.

According to the invention there is further provided a pharmaceutical composition comprising an antibody format of the invention and a pharmaceutically acceptable carrier or excipient.

Specifically, the pharmaceutical composition is provided for use in the treatment or prevention of a B-cell disorder.

According to the invention there is further provided a method for the treatment or prevention of a B-cell disorder comprising administering a therapeutically effective amount of the pharmaceutical composition to a subject in need thereof.

According to another aspect, there is further provided a diagnostic reagent or kit comprising the antibody format of the invention, to target B-cells in a sample, and optionally further comprising diagnostic reagents or tools, e.g. a label, to determine the quantity and/or quality of B-cells causing a B-cell disorder. Suitable assays are immunoabsorbent assays, such as ELISA. The antibody according to the invention may be conjugated to other molecules which allow the simple detection of said conjugate in, for instance, binding assays (e.g. ELISA) and binding studies.

Yet, according to a specific embodiment, the antibody format according to the invention is conjugated to a label or reporter molecule, e.g. selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Antibodies conjugated to labels or reporter molecules may be used, for instance, in assay systems or diagnostic methods.

According to a further aspect, there is provided a diagnostic method, i.e. a method to determine B-cells in a sample, employing the antibody format of the invention.

The sample may be a sample of bodily fluids, including blood, serum or urine.

According to another aspect, there is further provided a nucleic acid sequence encoding the antibody format of the invention.

According to another aspect, there is further provided a vector comprising the nucleic acid sequence of the invention.

According to another aspect, there is further provided a host cell comprising the nucleic acid sequence of the invention or a vector of the invention.

According to another aspect, there is further provided a method of producing an antibody format of the invention, comprising cultivating or maintaining a host cell of the invention under conditions such that said host cell produces the antibody format.

FIGURES

FIG. 1: Recombinant bispecific Fab-single chain (herein also called bsFabXsc or NA-C20 for the chimeric version and Novotarg for the humanized version), which contains a Fab linked to a scFv using a monomeric $CH_2$ domain as a linker.

Schematic description of an exemplary antibody format of the invention: The bispecific CD20 X CD95 antibody format is provided for the selective stimulation of the death receptor CD95 on the surface of normal, activated or malignant B cells expressing both, CD20 and CD95.

The sequence of this antibody, including those of the CD20 (2H7, murine, chimeric and humanized) and CD95 antibodies (murine, chimeric and humanized) are provided in FIG. 2E. The genetic construct encoding the antibody was stably transfected into Sp2/0 cells using standard techniques. The protein was purified from supernatants of transfected cells using affinity chromatography with KappaSelect resin, purchased from GE-Healthcare, Chalfont St Giles, UK.

FIG. 2: Sequence of exemplary antibody formats as referred to in the Examples.

FIG. 2A: Mouse VL and VH sequences (SEQ ID 1 and 5, respectively) of an antibody format with a binding site directed to CD95, CDR sequences are underlined (CDR1, CDR2, CDR3 of VL: SEQ ID 2-4; CDR1, CDR2, CDR3 of VH: SEQ ID 6-8).

FIG. 2B: VL and VH sequences (SEQ ID 9 and 10, respectively) of an antibody format with a binding site directed to CD95 (humanized), CDR sequences are underlined.

FIG. 2C: VL and VH sequences (SEQ ID 11 and 15, respectively) of an antibody format with a binding site directed to CD20 (murine, derived from the antibody 2H7 as described by Liu et al. The Journal of Immunology 139, 3521-3526 (1987), NCBI Accession M17953 and M17954), CDR sequences are underlined (CDR1, CDR2, CDR3 of VL: SEQ ID 12-14; CDR1, CDR2, CDR3 of VH: SEQ ID 16-18).

FIG. 2D: VL and VH sequences (SEQ ID 19 and 20, respectively) of an antibody format with a binding site directed to CD20 (humanized, derived from the antibody 2H7), CDR sequences are underlined.

FIG. 2E: Exemplary bispecific antibody formats CD95xCD20, chimeric and humanized versions:

SEQ ID 21: amino acid sequence of the chimeric version, light chain;

SEQ ID 22: nucleotide sequence of the chimeric version, light chain;

SEQ ID 23: amino acid sequence of the chimeric version heavy chain;

SEQ ID 24: linker sequence;

SEQ ID 25: nucleotide sequence of the chimeric version, heavy chain;

SEQ ID 26: amino acid sequence of the humanized version light chain;

SEQ ID 27: nucleotide sequence of the humanized version, light chain;

SEQ ID 28: amino acid sequence of the humanized version heavy chain;

SEQ ID 29: nucleotide sequence of the humanized version, heavy chain.

Figure 3:
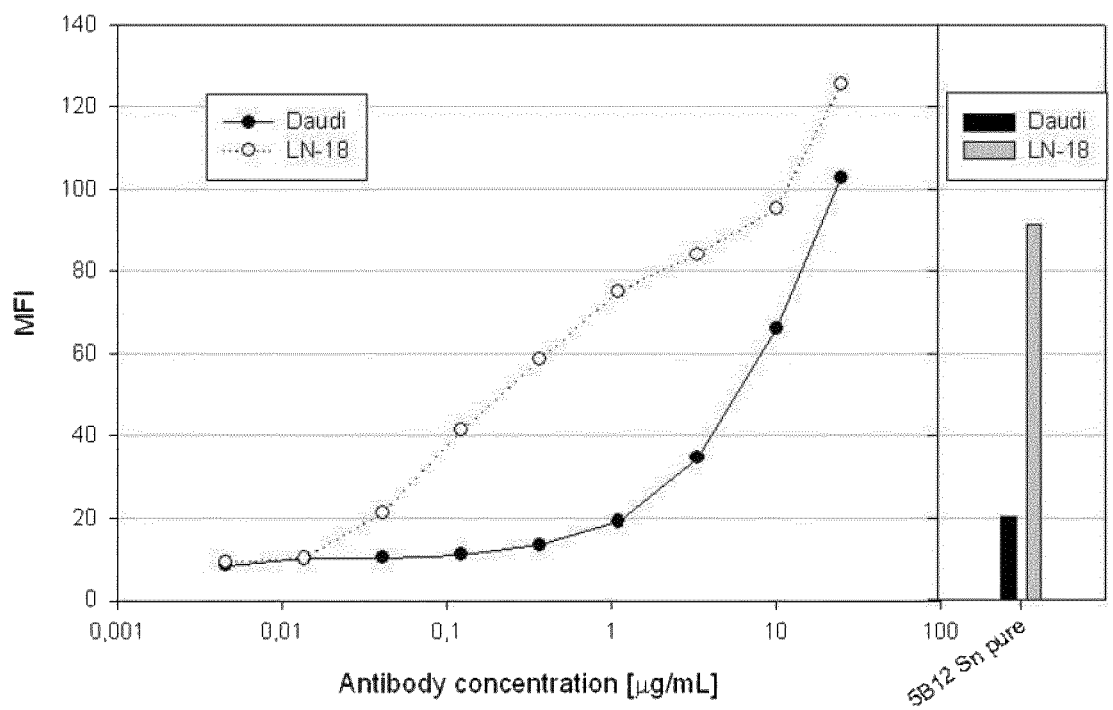

FIG. 3: Binding specificity of NA-C20 for CD20 and CD95 Flow cytometry analysis of $CD95^-/CD20^+$ Daudi cells (●) and $CD95^+/CD20^-$ LN-18 (○) cells after incubation with the indicated concentrations of purified NA-C20 (chimeric CD95XCD20 antibody derivative). This was compared to the binding of the antibody in the undiluted supernatant from clone 5B12 (expressing NA-C20). Detection antibody: goat α human Fcγ-PE, Jackson Immuno Research 109-116-098.

Figure 4:
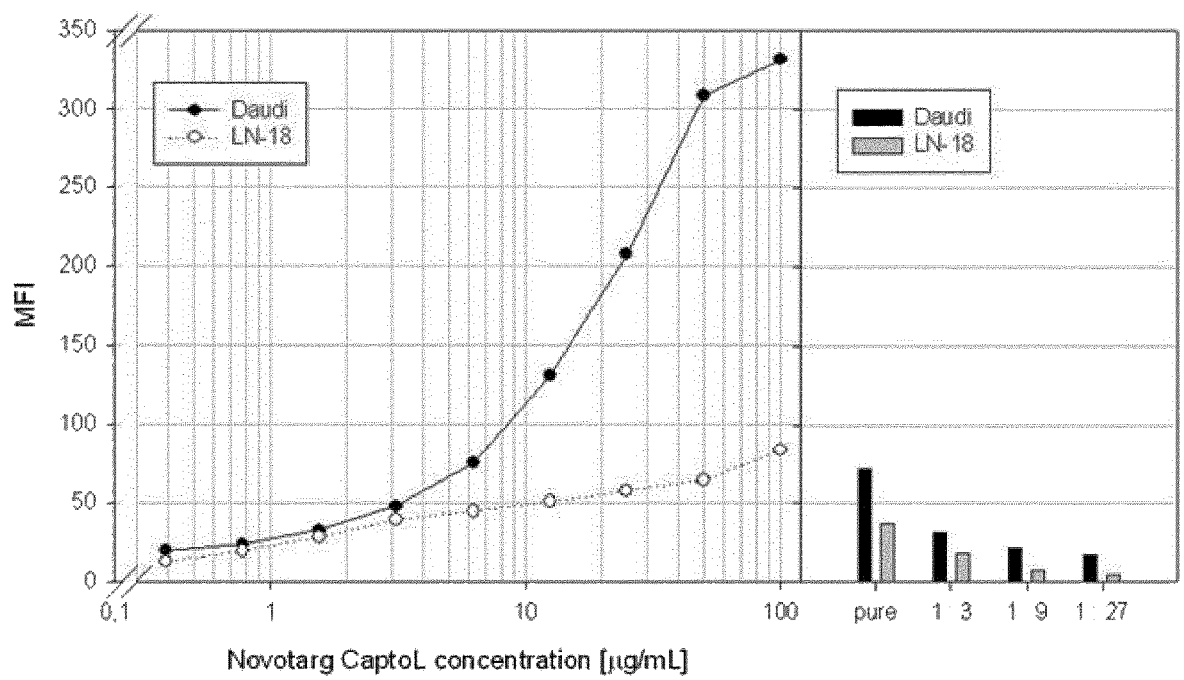

FIG. 4: Binding specificity of Novotarg for CD20 and CD95

Flow cytometry analysis of $CD95^-/CD20^+$ Daudi cells (●) and $CD95^+/CD20^-$ LN-18 cells (○) after incubation with the indicated concentrations of purified Novotarg (humanized CD95XCD20 antibody derivative). This was compared to the binding of the antibody in the indicated dilutions of supernatant from clone 25-CHO-S/BV004/K44 (expressing Novotarg). Detection antibody: goat α human Fcγ-PE, Jackson Immuno Research 109-116-098.

Figure 5:
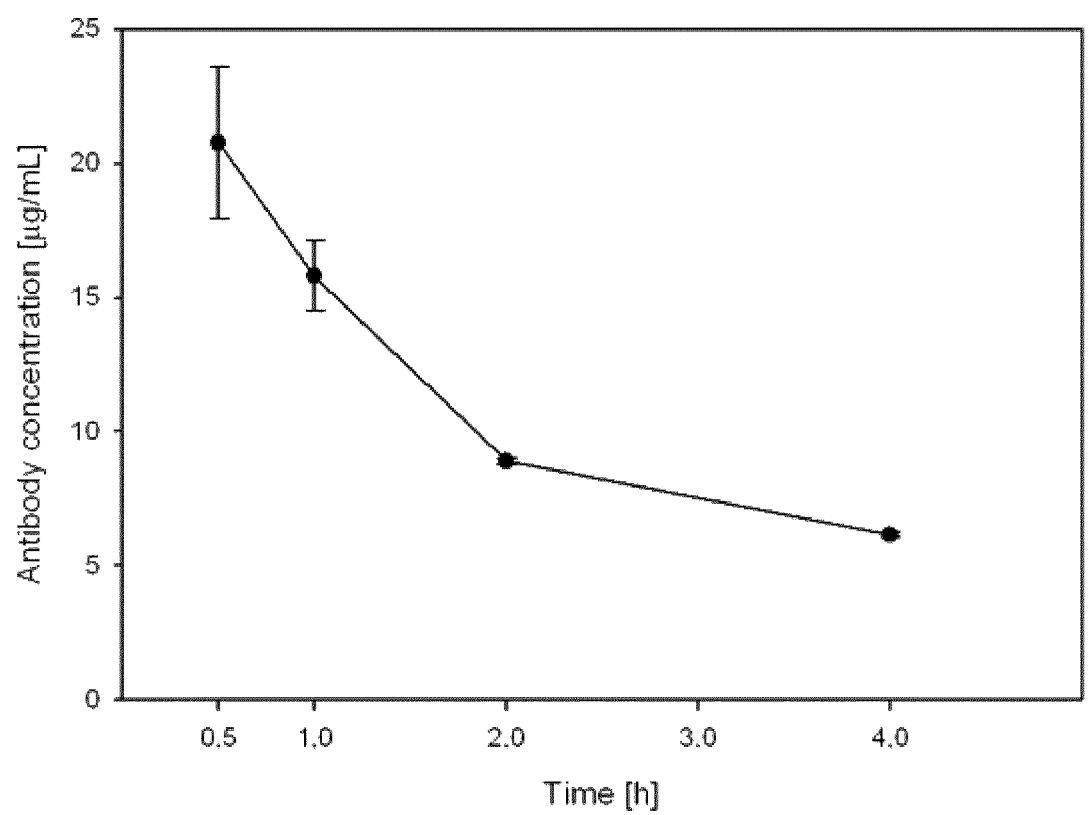

FIG. 5: In vivo half-life of chimeric CD95XCD20 antibody derivative C57BL6 (male, 6 weeks old) were injected with 50 μg of NA-C20 and blood samples were taken at 0.5 h, 1.0 h, 2.0 h and 4.0 h. Serum was incubated with SKW 6.4 cells, which were then analysed for bound antibody in flow cytometry (detection antibody: PE-goat anti human Fcγ, Jackson Immuno Research).

Figure 6:
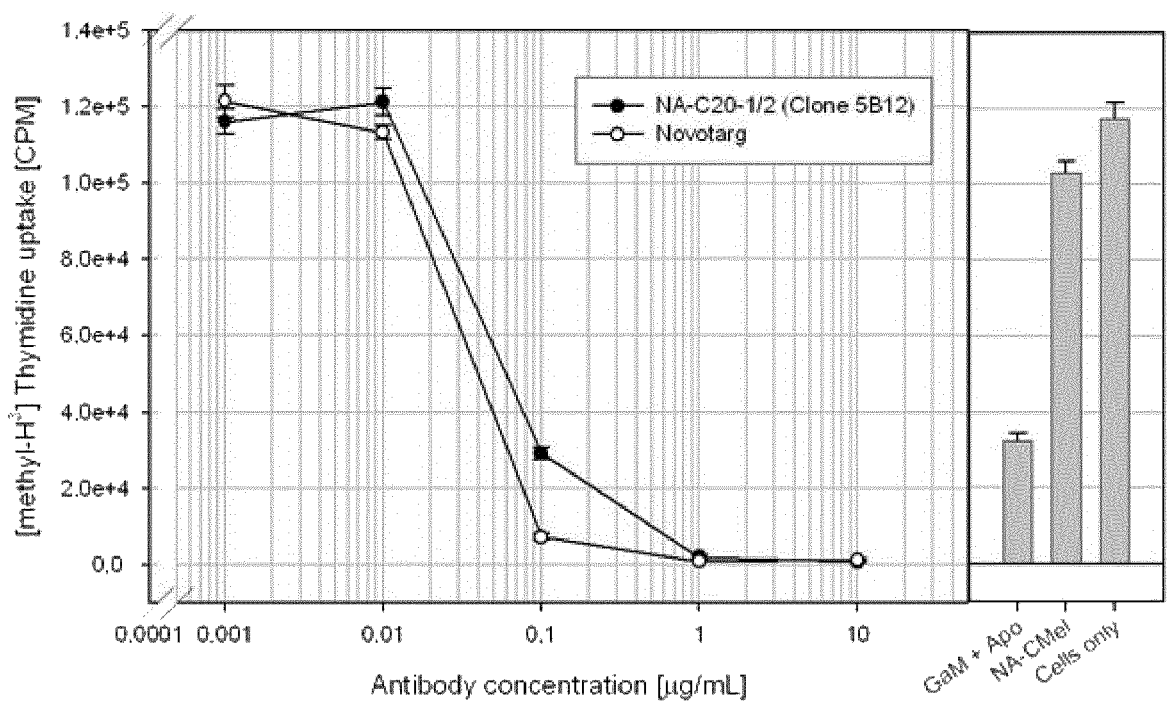

FIG. 6: Ability of NA-C20 and Novotarg to activate CD95 in $CD95^+/CD20^+0$ cells Thymidine incorporation assay with $CD95^+/CD20^+$ SWK 6.4 cells after incubation with the indicated concentrations of NA-C20 (●) or Novotarg (○). Non-treated cells served as negative control (column cells only), cells incubated with a mouse mAb against Apo-1 (cross-linked by a goat anti mouse Ab) served as a positive control (column GaM+Apo).

Figure 7:
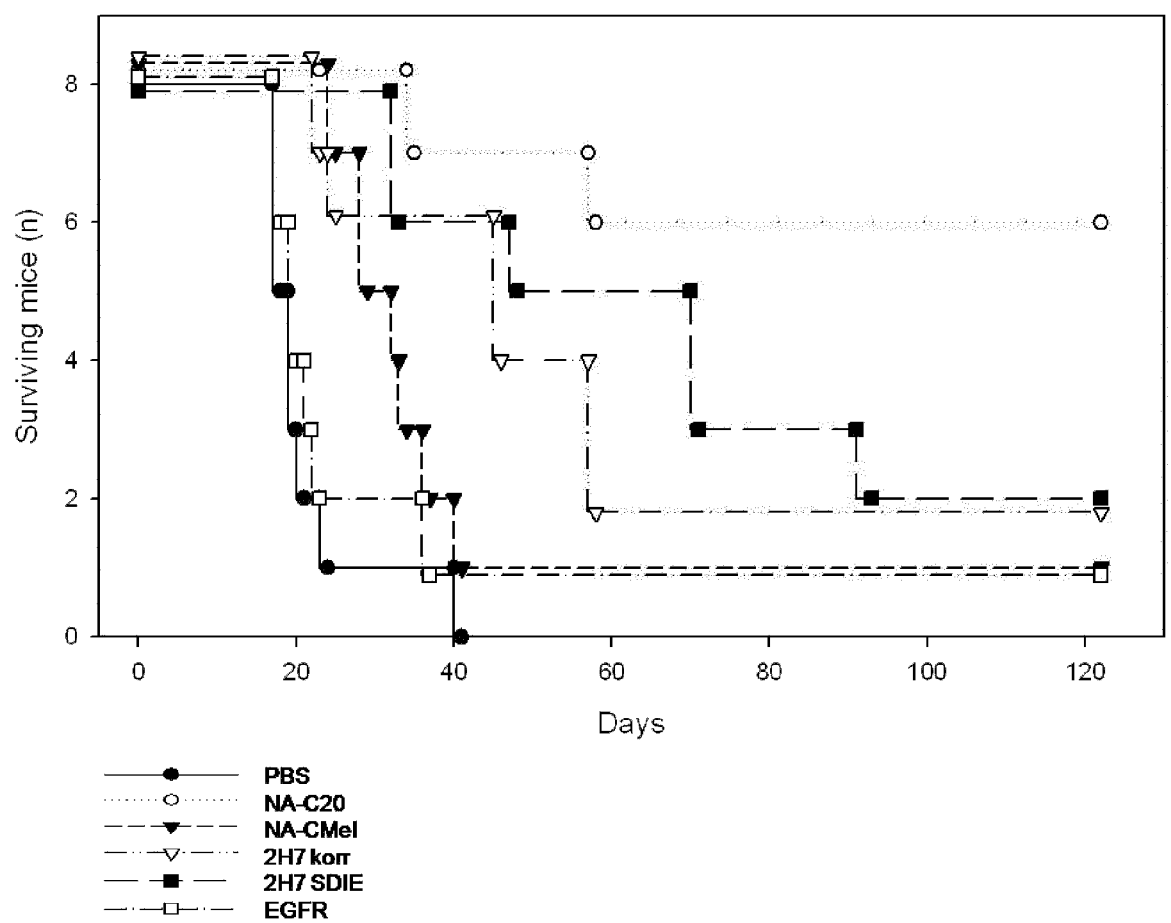

FIG. 7: Test of NA-C20 in a SCID mouse model

Eight SCID mice were injected with a lethal dose of $CD20^+/CD95^+$ B-lymphoblastoid cell line SKW 6.4 at day 0. In the following, mice were injected repeatedly with either 20 μg of NA-C20 (○), NA-CMeI (▼) or 100 μl PBS (●) at days 1, 2 and 3 after tumor cell inoculation, or once at day 1 after tumor cell inoculation with 60 μg of chimeric antibodies against CD20 (■, ▽) and an antibody directed against EGFR (epithelial growth factor receptor, □), respectively.

DETAILED DESCRIPTION

The term "antibody format" as used herein shall refer to polypeptides or proteins that consist of or comprise antibody domains, which are understood as constant and/or variable domains of the heavy and/or light chains of immunoglobulins, with or without a linker sequence. The antibody format of the invention is of a specific structure, specifically comprising a binding site of a Fab fragment consisting of a VL/VH domain pair and constant antibody domains, such as CL/CH1 domains, and further comprises a binding site of a scFv, which is linked to the scFv by a CH2 domain.

An antibody digested by papain yields three fragments: two Fab fragments and one Fc fragment. The term "Fab" is herein understood to include Fab, F(ab) or F(ab'), which may or may not include a hinge region. The Fab fragment is an antibody structure that still binds to antigens but is monovalent with no Fc portion.

Antibody domains may be of native structure or modified by mutagenesis or derivatization, e.g. to modify the antigen binding properties or any other property, such as stability or functional properties, such as binding to the Fc receptors FcRn and/or Fc gamma receptor. Polypeptide sequences are considered to be antibody domains, if comprising a beta-barrel structure consisting of at least two beta-strands of an antibody domain structure connected by a loop sequence.

The term "antibody format" shall particularly refer to polypeptides or proteins that exhibit the bispecific-binding properties, i.e. to the target antigens CD20 and CD95.

Exemplary antibody formats have a specific structure as depicted in FIG. 1. It may, be composed of a Fab fragment, a CH2 domain and a single chain Fv(scFv) fragment, in particular a scFv in VH/VL orientation. The antibody molecule may have a main chain in which the CH2 domain is coupled via its N-terminus to the heavy chain CH1 and VH domains of a Fab fragment and via its C-terminus to an scFv fragment.

It may as well comprise a main chain in which the CH2 domain is linked to the light chain of a Fab fragment, i.e. in which the main chain includes a VL and a CL domain, a hinge region, a CH2 domain and a single chain Fv fragment.

A further example refers to an antibody format in which the main chain includes a VL and a CH1 domain, a hinge region, a CH2 domain and an scFv fragment. A second chain of lower weight includes a VH and a CL domain. In such antibody format the Fab fragment is thus not a "classical (naturally occurring)" Fab fragment in which the variable domain of the light and the heavy chain are fused to its respective constant domain (CL or CH1, respectively) but a "hybrid" Fab fragment in which the variable domain is fused to the constant domain of the "opposite chain, i.e. the VH domain is fused to the CL domain and the VL domain is fused to the CH1 domain.

According to a further example, the antibody format comprises a molecule with a main chain in which the CH2 domain is linked to a CL and a VH domain. A second chain of lower weight includes a VL and a CH1 domain.

Yet, according to a further example, the antibody format comprises a molecule, comprising modifications in the hinge and CH2 domain, e.g. to obtain a monomeric CH2 domain, e.g. a CH2 domain in which amino acids in the CH2 domain and/or the hinge region have been modified, e.g. the cystein residues forming inter-chain disulfide bonds (C226 and/or C229 in human IgG-antibodies, the numbering of amino acids as provided herein is in line with the Kabat numbering [EU-Index]) are exchanged to prevent formation of dimers. Exemplary point mutations are C226S and C229S. In one embodiment a disulphide bond between the hinge domain of the first main chain and a hinge domain of the second main chain is defined by at least one of a cysteine residue at sequence position 226 and a cysteine residue at sequence position 229 of one of the hinge domains, according to the Kabat numbering [EU-Index].

An exemplary antibody format comprises an amino acid sequence of SEQ ID 26 (light chain) and SEQ ID 28 (heavy chain).

A further example refers to modification to obtain reduction of possible ADCC and/or CDC activity, e.g. by a switch of IgG1 to IgG2 subtype, e.g. by E233P and/or L234V and/or L235A and/or G236 deletion.

Further examples refer to a modification to reduce systemic activation, e.g. by a reduced binding to the Fc-receptor, such as D265G and/or A327Q and/or A330A.

Further examples refer to a modification to reduce immunogenicity, e.g. by a K.O. glycosylation site, such as N297Q, which provides for an impaired binding to lectin receptor.

The term "antibody format" shall specifically include antibody format in the isolated form, herein understood to be substantially free of other antibody formats directed against different target antigens or comprising a different structural arrangement of antibody domains. Still, an isolated antibody format as used according to the invention may be comprised in a combination preparation, containing a combination of the isolated antibody format, e.g. with at least one other antibody format, such as monoclonal antibodies or antibody fragments having different specificities.

The antibody format as used herein may be a recombinant bispecific antibody format, which term includes all antibody formats that are prepared, expressed, created or isolated by recombinant means, such as antibodies originating from animals, e.g. mammalians including human, that comprises genes or sequences from different origin, e.g. chimeric, humanized antibodies, or hybridoma derived antibodies. Further examples refer to antibody formats isolated from a host cell transformed to express the antibody format, or antibody formats isolated from a recombinant, combinatorial library of antibodies or antibody domains, or antibody formats prepared, expressed, created or isolated by any other means that involve splicing of antibody gene sequences to other DNA sequences.

It is understood that the term "antibody format" includes derivatives thereof. A derivative is any combination of one or more antibody domains or antibody formats of the invention and or a fusion protein in which any domain of the antibody format of the invention may be fused at any position of one or more other proteins, such as other antibodies or antibody formats, e.g. a binding structure comprising CDR loops, a receptor polypeptide, but also ligands, scaffold proteins, enzymes, toxins and the like. A derivative of the modular antibody of the invention may also be obtained by association or binding to other substances by various chemical techniques such as covalent coupling, electrostatic interaction, di-sulphide bonding etc. The other substances bound to the immunoglobulins may be lipids, carbohydrates, nucleic acids, organic and inorganic molecules or any combination thereof (e.g. PEG, prodrugs or drugs). In a specific embodiment of the present invention, the antibody format of the invention is a derivative comprising an additional tag allowing specific interaction with a biologically acceptable compound. There is not a specific limitation with respect to the tag usable in the present invention, as far as it has no or tolerable negative impact on the binding of the antibody format to its targets. Examples of suitable tags include His-tag, Myc-tag, FLAG-tag, Strep-tag, Calmodulin-tag, GST-tag, MBP-tag, and S-tag.

The term derivative also includes fragments, variants, analogs or homologs of antibody formats or antibody formats with a specific glycosylation pattern, e.g. produced by glycoengineering, which are functional and may serve as functional equivalents, e.g. binding to the specific targets and with functional properties, such as activity to target B-cells, e.g. apoptotic activity. The preferred derivatives still are functionally active with regard to the antigen binding, preferably with an apoptotic activity.

The term "glycoengineered" with respect to antibody sequences shall refer to glycosylation variants having modified immunogenic properties, ADCC and/or CDC as a result of the glycoengineering. All antibodies contain carbohydrate structures at conserved positions in the heavy chain constant regions, with each isotype possessing a distinct array of N-linked carbohydrate structures, which variably affect protein assembly, secretion or functional activity. IgG1 type antibodies are glycoproteins that have a conserved N linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5: 813-822 (1995). Removal of N-Glycan at N297, eg through mutating N297, e.g. to A, or T299 typically results in aglycosylated antibody formats with reduced ADCC.

Major differences in antibody glycosylation occur between cell lines, and even minor differences are seen for a given cell line grown under different culture conditions. Expression in bacterial cells typically provides for an aglycosylated antibody.

Antibody formats according to the present invention are specifically devoid of an active Fc moiety, thus, either composed of antibody domains that do not have an FCGR binding site, specifically including any antibody formats devoid of a chain of CH2 and CH3 domains, or comprising antibody domains lacking Fc effector function, e.g. by modifications to reduce Fc effector functions, in particular to abrogate or reduce ADCC and/or CDC activity. Such modifications may be effected by mutagenesis, e.g. mutations in the FCGR binding site or by derivatives or agents to interfere with ADCC and/or CDC activity of an antibody format, so to achieve reduction of Fc effector function or lack of Fc effector function, which is typically understood to refer to Fc effector function of less than 10% of the unmodified (wild-type) format, preferably less than 5%, as measured by ADCC and/or CDC activity.

The term "B-cell disorder" as used herein refers to a variety of disorders, including, but not limited to, B-cell malignancies, autoimmune disorders, B-cell lymphomas, B-cell leukemias, and other disorders. Specific examples of autoimmune disorder are selected from the group consisting of systemic lupus erythematosus, Sjögren's syndrome, scleroderma, rheumatoid arthritis, juvenile idiopathic arthritis, graft versus host disease, dermatomyositis, type I diabetes mellitus, Hashimoto's thyroiditis, Graves's disease, Addison's disease, celiac disease, Crohn's Disease, pernicious anaemia Pemphigus vulgaris, Vitiligo, autoimmune haemolyticanaemia, idiopathic thrombocytopenic purpura, giant cell arteritis, Myasthenia gravis, multiple sclerosis (MS), preferably relapsing-remitting MS (RRMS), glomerulonephritis, Goodpasture's syndrome, bullous pemphigoid, colitis ulcerosa, Guillain-Barré syndrome, chronic inflammatory demyelinating polyneuropathy, Anti-phospholipid syndrome, narcolepsy, sarcoidosis, and Wegener's granulomatosis.

The antibody format according to the present invention allows the modulation of the B cell repertoire to reduce autoreactivity of B cells. The modulation is more specific than that achieved by monospecific antibodies, since only activated B cell expressing CD95 and not resting B cells lacking it are affected. It could be shown that the antibody format according to the invention induced apoptosis of activated B-cells, and further suppressed activation induced IgG production and inhibited IgG synthesis of activated B-cells. Thus, auto-reactive B-cells producing IgG antibodies directed against autoimmune targets, such as auto-antigens, may be effectively reduced.

By the bispecific antibody format of the present invention not only malignant B cells, but also activated normal (benign) B cells that express the CD95 death receptor could be targeted and depleted. In contrast, resting B cells were not targeted, no effect could be seen with such normal B cells. This indicates that activated B cells are CD95 sensitive to undergo apoptotic cell death after incubation with the antibody format of the invention.

Depleting activated B cells suppresses antibody production. This was surprising, because the terminally differentiated antibody-producing cells, i.e. plasma cells, do not express CD20. Suppressing the activated precursor B cells is obviously sufficient to suppress antibody production.

Suppressing antibody production by the bispecific antibody formats of the invention is preferable over the use of established monospecific CD20 antibodies like rituximab (Rituxan®), which depletes all CD20 expressing B cells, without differentiating autoreactive or activated B cells from normal or resting B cells.

The term "binding site" as used herein with respect to an antibody or antibody format according to the present invention refers to a molecular structure capable of binding interaction with an antigen. Typically the binding site is located within the complementary determining region (CDR) of an antibody, herein also called "a CDR binding site", which is a specific region with varying structures conferring binding function to various antigens. The varying structures can be derived from natural repertoires of antibodies, e.g. murine or human repertoires, or may be recombinantly or synthetically produced, e.g. by mutagenesis and specifically by randomization techniques. These include mutagenized CDR regions, loop regions of variable antibody domains, in particular CDR loops of antibodies, such as CDR1, CDR2 and CDR3 loops of any of VL and/or VH antibody domains. The antibody format as used according to the invention typically comprises one or more CDR binding sites, each specific to an antigen.

The term "specific" or "bispecific" as used herein shall refer to a binding reaction which is determinative of the cognate ligand of interest in a heterogeneous population of molecules. Thus, under designated conditions, e.g. immunoassay conditions, the antibody format that specifically binds to its particular target does not bind in a significant amount to other molecules present in a sample.

A specific binding site is typically not cross-reactive with other targets. Still, the specific binding site may specifically bind to one or more epitopes, isoforms or variants of the target, or be cross-reactive to other related target antigens, e.g., homologs or analogs.

The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The bispecific antibody format of the present invention specifically comprises two sites with specific binding properties, wherein two different target antigens are recognized by the antibody format. Thus, an exemplary bispecific antibody format may comprise two binding sites, wherein each of the binding sites is capable of specifically binding a different antigen, e.g. a death receptor and a cell surface antigen of a B-cell.

The term "monovalent" as used herein with respect to a binding site of an antibody or antibody format shall refer to a molecule comprising only one binding site directed against a target antigen. The term "valency" is thus understood as the number of binding sites directed against the same target antigen, either specifically binding the same or different epitopes of an antigen.

The antibody format of the present invention is understood to comprise a monovalent binding site specifically binding a death receptor target and another monovalent binding site to specifically bind a cell surface antigen expressed on B-cells, in particular autoreactive B-cells.

The term "antigen" as used herein interchangeably with the terms "target" or "target antigen" shall refer to a whole target molecule or a fragment of such molecule recognized by an antibody binding site. Specifically, substructures of an antigen, e.g. a polypeptide or carbohydrate structure, generally referred to as "epitopes", e.g. B-cell epitopes or T-cell epitope, which are immunologically relevant, may be recognized by such binding site. The term "epitope" as used herein shall in particular refer to a molecular structure which may completely make up a specific binding partner or be part of a specific binding partner to a binding site of an antibody format of the present invention. An epitope may either be composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding the polypeptide to form a tertiary structure and the amino acids are not necessarily adjacent to one another in the linear sequence.

The term "cell surface antigen" with respect to a B-cell as used herein shall refer to an antigen expressed on the surface of a B cell, preferably a mature, activated or auto-reactive B-cell that can be targeted with an antagonist that binds thereto. CD20 is considered an exemplary B-cell surface marker targeted by the antibody format of the present invention.

A binding site specifically binding to CD20 may be derived from a commercially available monoclonal antibody directed against the antigen, e.g. rituximab or ocrelizumab directed against CD20. Specifically a binding site derived from any of the anti-CD20 antibody formats as exemplified in FIG. 2 may be used.

The term "CD20" includes any variants, isoforms and species homologs of human CD20 which are naturally expressed by cells or are expressed on cells transfected with the CD20 gene.

The term "death receptor" herein interchangeably used with the term "CD95" as used herein shall refer to an antigen derived from a receptor on the surface of cells that leads to programmed cell death by one or more apoptosis pathways. It turned out that in contrast to activated B cells, CD95 is not expressed on normal resting B cells.

CD95 is also known as Fas or Apo-1, and member of the tumor necrosis factor receptor superfamily. A binding site specifically binding to CD95 may be derived from antibodies directed to CD95, such as the clones APO-1 or LT95 and DX 2 distributed by Acris Antibodies, Herford, Germany. Specifically a binding site derived from any of the anti-CD95 antibody formats as exemplified in FIG. 2 may be used.

The term "CD95" includes any variants, isoforms and species homologs of human CD95 which are naturally expressed by cells or are expressed on cells transfected with the CD95 gene.

The term "variants" shall refer to mutants, e.g. obtained by site-directed mutagenesis methods, in particular to delete, exchange, introduce inserts into a specific antibody region or chemically derivatize an amino acid sequence, in the constant domains to engineer the antibody effector function or half-life, or in the variable domains to improve antigen-binding properties, e.g. by affinity maturation techniques. Any of the known mutagenesis methods may be employed, including point mutations at desired positions, e.g. obtained by randomisation techniques. In some cases positions are chosen randomly, e.g. with either any of the possible amino acids or a selection of preferred amino acids to randomise the antibody sequences. The term "variant" shall specifically encompass functionally active variants.

The term "functionally active variant" of a molecule, such as the antibody as used herein, means a sequence resulting from modification of this sequence (a parent sequence) by insertion, deletion or substitution of one or more amino acids, or chemical derivatization of one or more amino acid residues, or nucleotides within the sequence or at either or both of the distal ends of the sequence, and which modification does not affect (in particular impair) the activity of this sequence. In the case of a binding site having specificity to a selected target antigen, the functionally active variant of a molecule would still have the predetermined binding specificity, though this could be changed, e.g. to change the fine specificity to a specific epitope, the affinity, the avidity, the Kon or Koff rate, etc.

Functionally active variants may be obtained by changing the sequence of a parent antibody format, e.g. any of the sequences of FIG. 2, e.g. the NA-C20 or Novotarg sequences of FIG. 2E i) or ii), and are characterized by having a biological activity similar to that displayed by the respective sequence, including the ability to bind CD20 and/or CD95 or to target activated or auto-reactive B-cells.

The functionally active variant of the antibody format preferably has substantially the same biological activity, as determined by a specific binding assay or functional test to target activated or auto-reactive B-cells. The term "substantially the same biological activity" as used herein refers to the activity as indicated by substantially the same activity being at least 50%, at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the activity as determined for the parent antibody format, e.g. the recombinant bispecific antibody format NA-C20 or Novotarg of FIG. 2E.

In a preferred embodiment the functionally active variant
a) is a biologically active fragment of the molecule, the fragment comprising at least 50% of the sequence of the molecule, preferably at least 70%, more preferably at least 80%, still more preferably at least 90%, even more preferably at least 95% and most preferably at least 97%, 98% or 99%;

b) is derived from the molecule by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the molecule or a functionally active variant thereof and additionally at least one amino acid or nucleotide heterologous to the polypeptide or the nucleotide sequence, preferably wherein the functionally active variants are derived from any of the naturally occurring or recombinant anti-CD19, anti-CD20, anti-CD40 and/or anti-CD95 antibodies.

In one preferred embodiment of the invention, the functionally active variant of the antibody according to the invention is essentially identical to the variant described above, but differs from its polypeptide or the nucleotide sequence, respectively, in that it is derived from a homologous sequence of a different species. These are referred to as naturally occurring variants.

The invention specifically provides for chimeric, humanized or human sequences and functionally active variants of a parent antibody format comprising such chimeric, humanized or human sequences.

The term "chimeric" as used with respect to an antibody format of the invention refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "humanized" as used with respect to an antibody format of the invention refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "human" as used with respect to an antibody format of the invention, is understood to include antibodies having variable and constant regions derived from human germline immunoglobulin sequences. The human antibody formats of the invention may include amino acid residues not encoded by human germline immunoglobulin sequences (e.g., mutations introduced by random or site-specific mutagenesis in vitro or by somatic mutation in vivo), for example in the CDRs. Human antibody formats of the invention include antibodies isolated from human immunoglobulin libraries or from animals transgenic for one or more human immunoglobulin.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains a function of the unaltered polypeptide or the nucleotide sequence, when used in combination of the invention. Such sequence alterations can include, but are not limited to, (conservative) substitutions, additions, deletions, mutations and insertions.

A CDR variant includes an amino acid sequence modified by at least one amino acid, wherein said modification can be chemical or a partial alteration of the amino acid sequence, which modification permits the variant to retain the biological characteristics of the unmodified sequence. For example, the variant is a functional variant which binds to CD19, CD20, CD40 or CD95. A partial alteration of the CDR amino acid sequence may be by deletion or substitution of one to several amino acids, e.g. 1, 2, 3, 4 or 5 amino acids, or by addition or insertion of one to several amino acids, e.g. 1, 2, 3, 4 or 5 amino acids, or by a chemical derivatization of one to several amino acids, e.g. 1, 2, 3, 4 or 5 amino acids, or combination thereof. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;

Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

"Percent (%) amino acid sequence identity" with respect to the polypeptide sequences identified herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

The term "subject" as used herein shall refer to a warm-blooded mammalian, particularly a human being. In particular the medical use format of the invention or the respective method of treatment applies to a subject in need of prophylaxis or treatment of a B-cell disorder or a disease condition associated with a B-cell disorder. The subject may be a patient suffering from early stage or late stage disease, or else subject predisposed of such disease, e.g. by genetic predisposition.

According to a specific embodiment, the antibody formats of the invention have apoptotic activity, i.e. direct cytotoxic activity against the target B-cells independent of immune-effector cells, such as NK cells. Specifically, the antibody formats of the invention have apoptotic activity, as measured in a standard apoptosis assay, e.g. as measured in a standard DNA fragmentation assay.

The apoptotic activity is preferably measured using standard methods of determining dying and/or dead cells. In order to measure apoptosis, cytotoxicity assays can be employed. These assays can be radioactive and non-radioactive assays that measure increases in plasma membrane permeability, since dying cells become leaky, or colorimetric assays that measure reduction in the metabolic activity of mitochondria. Mitochondria in dead cells cannot metabolize dyes, while mitochondria in live cells can.

One can also measure early indicators for apoptosis such as alterations in membrane asymmetry resulting in occurrence of phosphatidylserine on the outside of the cell surface (Annexin V based assays). Alternatively, later stages of apoptosis, such as activation of caspases can be measured in populations of cells or in individual cells. In addition, measurement of release of cytochrome C and AIF into cytoplasm by mitochondria or fragmentation of chromosomal DNA can be determined.

Terminal deoxynucleotidyl transferase dUTP nick end labeling (TUNEL) is a common method for detecting DNA fragmentation that results from apoptotic signaling cascades. The assay relies on the presence of nicks in the DNA which can be identified by terminal deoxynucleotidyl transferase, an enzyme that will catalyze the addition of bromolated dUTPs that are secondarily detected with a specific labelled antibody.

The preferred apoptotic activity of the antibody format according to the invention amounts to at least 20% of cytolysis, preferably at least 30%, more preferred at least 40%, even more preferred at least 50%, as measured in a respective ex vivo cell killing assay; e.g. measuring survival of B cells after incubation with bispecific antibodies by flow cytometry.

Specifically, the antibody format of the present invention is devoid of Fc effector function and would not have a significant cytotoxic activity in the presence of immune-effector cells as measured in a standard ADCC or CDC assay, e.g. employing cells expressing the receptor target on the cell surface.

The low cytotoxic activity as determined by either of an ADCC or CDC assay can be shown for any antibody format of the invention, if there is no significant increase in the percentage of cytolysis as compared to a control. The lack of Fc effector function is typically determined if the cytotoxic activity as measured by the absolute percentage increase of the ADCC and/or CDC activity, is preferably lower than 10%, preferably lower than 5%, more preferably lower than 3%.

Preferably, an antibody format is used that binds to one or both of the target antigens with a high affinity, in particular with a high on and/or a low off rate, or a high avidity of binding. The binding affinity of an antibody is usually characterized in terms of the concentration of the antibody, at which half of the antigen binding sites are occupied, known as the dissociation constant (Kd, or KD). Usually a binder is considered a high affinity binder with a $Kd<10^{-8}$ M, preferably a $Kd<10^{-9}$ M, even more preferred is a $Kd<10^{-19}$ M.

Yet, in an alternatively preferred embodiment the individual antigen binding affinities are of medium affinity, e.g. with a Kd of less than $10^{-6}$ M and up to $10^{-8}$ M, e.g. when binding to at least two antigens.

Bispecific monoclonal antibody formats of the invention can be produced by a variety of techniques, including recombinant antibody technology, optionally employing hybridoma or libraries of human antibody sequences. Recombinant antibody technology is preferred since it allows reproducible production by transfected cells and simplified purification.

The antibody formats of the present invention are specifically provided in a pharmaceutical composition. Pharmaceutical compositions are contemplated wherein the antibody format of the present invention and one or more therapeutically active agents are formulated. Stable formulations of the antibody formats of the present invention are prepared for storage by mixing the antibody format having the desired degree of purity optionally with pharmaceutically acceptable carriers, excipients or stabilizers, in the form of lyophilized formulations, aqueous solutions or oil-in-water emulsions Typically such compositions comprise a pharmaceutically acceptable carrier as known and called for by acceptable pharmaceutical practice, see e.g. Remingtons Pharmaceutical Sciences, 16th edition (1980) Mack Publishing Co. Examples of such carriers include sterilized carriers such as saline, Ringers solution or dextrose solution, optionally buffered with suitable buffers to a pH within a range of 5 to 8.

The formulations to be used for in vivo administration will need to be sterile. This is readily accomplished by filtration through sterile filtration membranes or other suitable methods.

Administration of the pharmaceutical composition comprising the antibody formats of the present invention may be done in a variety of ways, including systemic or parenteral administration, preferably in the form of a sterile aqueous solution, e.g. by the intravenous, intramuscular or subcutaneous route, but also orally, intranasally, intraotically, transdermally, mucosal, topically (e.g., gels, salves, lotions, creams, etc.), intraperitoneally, intramuscularly, intrapulmonary, vaginally, parenterally, rectally or intraocularly. Thus, the invention provides for the antibody format in a respective formulation suitable for such use.

The present invention includes a pharmaceutical preparation, containing as active substance the antibody formats of the invention in a therapeutically effective amount. In particular, a pharmaceutically acceptable formulation of the antibody format is compatible with the treatment of a subject in need thereof.

The term "therapeutically effective amount", used herein interchangeably with any of the terms "effective amount" or "sufficient amount" of the antibody format of the present invention, is a quantity or activity sufficient to, when administered to the subject effect beneficial or desired results, including clinical results, and, as such, an effective amount or synonym thereof depends upon the context in which it is being applied. In the context of disease, therapeutically effective amounts of the antibody format may be used to treat, modulate, attenuate, reverse, or affect a disease or condition that benefits from a down-regulation or reduction of excessive B-cells, e.g. for inhibition of autoimmune reactions, for example, acute or chronic inflammatory diseases associated with an auto-reactive B-cell disorder. An effective amount is intended to mean that amount of a compound that is sufficient to treat, prevent or inhibit such diseases or disorder. The amount of the antibody format that will correspond to such an amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

Moreover, a treatment or prevention regime of a subject with a therapeutically effective amount of the antibody format of the present invention may consist of a single administration, or alternatively comprise a series of applications. For example, the antibody format may be administered at least once a year, at least once a half-year or at least once a month. However, in another embodiment, the antibody format may be administered to the subject from about one time per week to about a daily administration for a given treatment. The length of the treatment period depends on a variety of factors, such as the severity of the disease, the age of the patient, the concentration and the activity of the antibody format. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

A therapeutically effective amount of the antibody format such as provided to a human patient in need thereof may specifically be in the range of 0.5-500 mg, preferably 1-400 mg, even more preferred up to 300 mg, up to 200 mg, up to 100 mg or up to 10 mg, though higher doses may be indicated e.g. for treating acute disease conditions.

Exemplary formulations as used for parenteral administration include those suitable for subcutaneous, intramuscular or intravenous injection as, for example, a sterile solution or suspension.

In one embodiment, the antibody format according to the present invention is the only therapeutically active agent administered to a patient, e.g. as a disease modifying monotherapy.

Alternatively, the antibody format according the present invention is administered in combination with one or more other therapeutic agents, including but not limited to standard treatment, e.g. chemotherapeutics in case of malignant disease, or interferon-beta or steroids in case of MS or high dose immunoglobulins in case of ITP.

A combination therapy is particularly employing a standard regimen, e.g. as used for treating RRMS. This may include interferon-beta or steroids.

In a combination therapy, the antibody format may be administered as a mixture, or concomitantly with one or more other therapeutic regimens, e.g. either before, simultaneously or after concomitant therapy.

The biological properties of the antibody format according to the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody format to be used as a therapeutic with the appropriate half-life, effector function, apoptotic activity and IgG inhibitory activity. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the antibody format according to the invention. Tests of the substances in humans are ultimately required for approval as drugs, and these experiments are contemplated herein. Thus the antibody format of the present invention may be tested in animal models or in humans to determine their therapeutic efficacy, toxicity, immunogenicity, pharmacokinetics, and/or other clinical properties.

Methods for producing and characterizing an antibody according to the invention are well-known in the art. In a preferred embodiment, antibody variants are produced and screened for predefined properties using one or more cell-based assays employing cells expressing the antibody format of the invention or in vivo assays. Such assays often involve monitoring the response of cells to the antibody, for example cell survival, cell death, change in cellular morphology, or transcriptional activation such as cellular expression of a natural gene or reporter gene.

These assays are typically based on the function of the antibody format; that is, the ability of the antibody format to bind the target antigens, e.g. on the same cell, and mediate some biochemical event, for example the apoptosis or inhibition of said cells e.g. in a competitive binding assay, B-cell binding inhibition or the reduction of IgG expression in the presence or absence of the antibody of the invention.

Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored.

Transcriptional activation may also serve as a method for assaying function in cell-based assays. In this case, response may be monitored by assaying for natural genes or immunoglobulins which may be upregulated, for example the release of certain interleukins may be measured, or alternatively the readout may be via a reporter construct. Cell-based assays may also involve the measure of morphological changes of cells as a response to the presence of an antibody according to the invention.

The recombinant production of the antibody format of the invention preferably employs an expression system, e.g. including expression constructs or vectors comprising a nucleotide sequence encoding the antibody format.

The term "expression system" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may then also be integrated into the host chromosome. Alternatively, an expression system can be used for in vitro transcription/translation.

"Expression constructs" or "vectors" used herein are defined as DNA sequences that are required for the transcription of cloned recombinant nucleotide sequences, i.e. of recombinant genes and the translation of their mRNA in a suitable host organism. Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences.

Specifically the term refers to a vehicle by which a DNA or RNA sequence (e.g. a foreign gene), e.g. a nucleotide sequence encoding the antibody format of the present invention, can be introduced into a host cell, so as to transform the host and promote expression (e.g. transcription and translation) of the introduced sequence. Plasmids are preferred vectors of the invention.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA that can readily accept additional (foreign) DNA and which can readily be introduced into a suitable host cell. A vector of the invention often contains coding DNA and expression control sequences, e.g. promoter DNA, and has one or more restriction sites suitable for inserting foreign DNA. Coding DNA is a DNA sequence that encodes a particular amino acid sequence for a particular polypeptide or protein such as an antibody format of the invention. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors of the invention will often include one or more replication systems for cloning or expression, one or more markers for selection in the host, e.g. antibiotic resistance, and one or more expression cassettes.

The procedures used to ligate DNA sequences, e.g. providing or coding for the factors of the present invention and/or the POI, a promoter, a terminator and further sequences, respectively, and to insert them into suitable vectors containing the information necessary for integration or host replication, are well known to persons skilled in the art, e.g. described by J. Sambrook et al., "Molecular Cloning 2nd ed.", Cold Spring Harbor Laboratory Press (1989).

The term "cell line" as used herein refers to an established clone of a particular cell type that has acquired the ability to proliferate over a prolonged period of time. The term "host cell line" refers to a cell line as used for expressing an endogenous or recombinant gene to produce polypeptides, such as the recombinant antibody format of the invention. A "production host cell line" or "production cell line" is commonly understood to be a cell line ready-to-use for cultivation in a bioreactor to obtain the product of a production process, the recombinant antibody format of the invention.

A host cell is specifically understood as a recombinant cell or cell line transfected with an expression construct, such as a vector according to the invention.

The term "recombinant" as used herein shall mean "being prepared by genetic engineering" or "the result of genetic engineering", e.g. specifically employing heterologous sequences incorporated in a recombinant vector or recombinant host cell.

A bispecific monoclonal antibody format of the invention may be produced using any known and well-established expression system and recombinant cell culturing technology, for example, by expression in bacterial hosts (prokaryotic systems), or eukaryotic systems such as yeasts, fungi, insect cells or mammalian cells. An antibody molecule of the present invention may be produced in transgenic organisms such as a goat, a plant or a XENOMOUSE transgenic mouse, an engineered mouse strain that has large fragments of the human immunoglobulin loci and is deficient in mouse antibody production. An antibody may also be produced by chemical synthesis.

According to a specific embodiment, the host cell is a production cell line of cells selected from the group consisting of CHO, PerC6, CAP, HEK, HeLa, NS0, SP2/0, hybridoma and Jurkat. More specifically, the host cell is obtained from CHO-K1, CHO-DG44 or CHO-S cells.

Chinese hamster ovary (CHO) cells have been most commonly used for antibody production. In addition to providing suitable glycosylation patterns, these cells allow consistent generation of genetically stable, highly productive clonal cell lines. They can be cultured to high densities in simple bioreactors using serum free media, and permit the development of safe and reproducible bioprocesses.

The host cell of the invention is specifically cultivated or maintained in a serum-free culture, e.g. comprising other components, such as plasma proteins, hormones, and growth factors, as an alternative to serum.

Host cells are most preferred, when being established, adapted, and completely cultivated under serum free conditions, and optionally in media which are free of any protein/peptide of animal origin.

The foregoing description will be more fully understood with reference to the following examples. Such examples are, however, merely representative of methods of practicing one or more embodiments of the present invention and should not be read as limiting the scope of invention.

EXAMPLES

Example 1: Production of the Bispecific Antibody Formation with Specificity for CD20 and CD90

Chimeric Version (Termed NA-C20)

The amino acid sequences encoding chimeric light chain (mouse anti CD95-VJ/human CL; SEQ ID 21) and chimeric heavy chain (mouse anti CD95-VDJ/human CH1/hinge/modified CH2/anti CD20 VHVL; SEQ ID 23) were successfully expressed in a SP2/0 cell line. The proteins are encoded by the nucleotide sequences SEQ ID 22 and SEQ ID 25, which assembled correctly to form the said bispecific anti CD95XCD20 antibody derivative. This was confirmed by detection with antibodies specific for human IgG1 and human kappa light chain in western blot. Protein for further characterization was purified from cell culture supernatant by affinity chromatography (CaptoL, GE Healthcare).

Humanized Version (Termed Novotarg)

The amino acid sequences encoding humanized CD95-VJ/human CL (SEQ ID 26) and humanized CD95-VDJ-CH1-H-CH/humanized CD20scFv (SEQ ID 28) were reverse translated into nt sequences and codon-optimized for *Cricetulus griseus*. The corresponding nucleotide sequences are listed as SEQ ID 27 and SEQ ID 29. Synthetic genes were designed, synthesised and cloned into an appropriate expression vector for the transfection of a Chinese hamster ovary (CHO) host cell line. Both sequences were expressed and assembled successfully to form the said bispecific antibody derivative. This was confirmed by detection with antibodies specific for human IgG1 and human kappa light chain in western blot. Protein for further characterization was purified from cell culture supernatant by affinity chromatography (CaptoL, GE Healthcare).

Example 2: Characterization of the Bispecific Antibody Formation with Specificity for CD20 and CD90

Binding Affinity of Chimeric CD95XCD20 Antibody Derivative Towards CD95 and CD20

Successful binding of the chimeric CD95XCD20 antibody derivative towards its targets was confirmed by flow cytometry (BD FACS Calibur). A CD20$^+$/CD95$^-$ B lymphoblast cell line (Daudi) and a CD20$^-$/CD95$^+$glioma cell line (LN-18) were incubated with a serial dilution of the chimeric antibody derivative (2×10$^6$ cells/sample in PBS 1% FCS 0.01% NaN$_3$, 1 h at 4° C.), respectively. Bound protein was detected with a PE-labelled goat anti human Fcγ-specific antibody (Jackson Immuno Research cat. no. 109-116-098, 1:200, 30 min at 4° C.). A concentration-dependent increase in mean fluorescent intensity (MFI) approved successful binding of the chimeric bispecific antibody to CD20 as well as to CD95 (FIG. 3).

Binding Affinity of Humanized CD95XCD20 Antibody Derivative Towards CD95 and CD20

Successful binding of the humanized CD95XCD20 antibody derivative towards its targets was confirmed by flow cytometry (BD FACS Calibur). A CD20$^+$/CD95$^-$ B lymphoblast cell line (Daudi) and a CD20$^-$/CD95$^+$glioma cell line (LN-18) were incubated with a serial dilution of the chimeric antibody derivative (2×10$^6$ cells/sample in PBS 1% FCS 0.01% NaN$_3$, 1 h at 4° C.), respectively. Bound protein was detected with a PE-labelled goat anti human Fcγ-specific antibody (Jackson Immuno Research cat. no. 109-116-098, 1:200, 30 min at 4° C.). A concentration-dependent increase in mean fluorescent intensity (MFI) approved successful binding of the humanized bispecific antibody to CD20 as well as to CD95 (FIG. 4).

In Vivo Half Life of the Chimeric CD95XCD20 Antibody Derivative C57BL6 mice (male, 6 weeks old, n=3) received 50 µg of the chimeric CD95XCD20 antibody derivative (NA-C20) intravenously (tail vein). Blood samples were taken at 0.5 h, 1.0 h, 2.0 h and 4.0 h post injection. Serum antibody concentration was measured by detection of antibody bound to CD20$^+$/CD95$^+$ B-lymphoblastoid cell line SKW 6.4 via flow cytometry (FIG. 5)

Example 3: In Vitro Proof of Concept for the Bispecific Antibody Formation with Specificity for CD20 and CD90

Potency of the CD95XCD20 Antibody Derivative

The potency to activate CD95 on CD20$^+$/CD95$^+$ B-cells was demonstrated for both the chimeric (NA-C20) and the humanized variant (Novotarg) on CD20$^+$/CD95$^+$ B-lymphoblastoid cell line SKW 6.4. Cells were incubated with a serial dilution of the CD95XCD20 antibody derivative and cell proliferation was determined by a thymidine incorporation assay. In brief, 3×10$^4$ cells per well were seeded into 96-well flat-bottom microtiter plates and the antibody derivative was added in the respective concentrations. After 24 h, [$^3$H]methyl-thymidine (purchased from Hartman analytics cat. no. MT6035/3) was added to the cells to achieve a final concentration of 0.5 µCi/well. After another 20 h of incubation, cells were harvested and the tritium incorporation was analyzed by liquid scintillation spectrometry (PerkinElmer liquid scintillation analyzer MicroBeta2). A dose dependent inhibition in proliferation could be observed, demonstrating the ability of NA-C20 and Novotarg to selectively stimulate death receptor CD95 in cells expressing both CD20 and CD95 (FIG. 6).

Example 4: In Vivo Proof of Concept for the Bispecific Antibody Formation with Specificity for CD20 and CD90

In Vivo Lymphoma SCID Mouse Model

Four to five weeks old SCID mice (Bosma et al., Nature 1983 Feb. 10; 301(5900):527-30) were injected intravenously (tail vein) with a lethal dose of 1×10$^7$ cells of CD20$^+$/CD95$^+$ B-lymphoblastoid cell line SKW 6.4 (n=8). At days 1, 2 and 3 post injection, eight mice received 20 µg of the chimeric CD95XCD20 antibody derivative (NA-C20) whereas the control groups received PBS or 20 µg NA- CMeI, respectively (i.p.). NA-CMeI is a bispecific antibody derivative with specificity for CD95 and a second, unrelated target (melanoma associated proteoglycan). Results are shown in FIG. 7. After 40 days all mice of the control group had died whereas seven mice had survived from the NA-C20 treated group. Six mice of this group were still alive after 120 days. This indicates effective depletion of the CD20+/CD95+ SKW 6.4 cells in these mice. In turn, seven out of eight mice of the NA-CMeI treated control group had died at day 40. NA-CMeI is obviously not capable of effective tumor cell depletion. In contrast to NA-C20, NA-CMeI has no other target specificity for proteins expressed on SKW6.4 cells than CD95, to which it binds monovalently. This prevents receptor cross-linking, which is a prerequisite for effective CD95 activation and apoptosis induction. NA-CMeI demonstrates the target cell-restricted mode of action of bispecific antibody derivatives with specificity for CD95. NA-C20 is therefore expected to be only effective on CD95+/CD20+ cells, leaving CD95+/CD20− cells, e.g. hepatocytes, unaffected. This ensures for selective targeting and reduced off-target effects (Jung et al., Cancer Res. 2001 Mar. 1; 61(5):1846-8).

The invention claimed is:

1. A bispecific antibody, which comprises
   a) a Fab fragment comprising a first binding site for a first antigen and a hinge region which is modified to exchange one or more cysteine residues that would form interchain disulfide bonds;
   b) an scFv fragment comprising a second binding site for a second antigen; and
   c) a monomeric CH2 domain, wherein the CH2 domain is bound via its N-terminus to a) the Fab fragment, and via its C-terminus to b) the scFv fragment, wherein the first antigen is CD95 and the second antigen is CD20; or the first antigen is CD20 and the second antigen is CD95; wherein the binding site that binds CD20 comprises six complementarity determining regions of antibody variable domains VL-CDR1-3 and VH-CDR1-3), wherein
   i) VL-CDR1 comprises the amino acid sequence RASSSVSYM (SEQ ID NO: 12);
   ii) VL-CDR2 comprises the amino acid sequence APSNLAS (SEQ ID NO: 13);
   iii) VL-CDR3 comprises the amino acid sequence QQWSFNPPT (SEQ ID NO: 14);
   iv) VH-CDR1 comprises the amino acid sequence SYNMH (SEQ ID NO: 16);
   v) VH-CDR2 comprises the amino acid sequence AIYPGNGDTSYNQKFKG (SEQ ID NO: 17); and
   vi) VH-CDR3 comprises the amino acid sequence VVYYSNSYWYFDV (SEQ ID NO: 18);
   and wherein the binding site that binds CD95 comprises six complementarity determining regions of variable antibody domains (VL-CDR1-3 and VH-CDR1-3), wherein
   i) VL-CDR1 comprises the amino acid sequence RASESVEYYGTSLMQ (SEQ ID NO: 2);
   ii) VL-CDR2 comprises the amino acid sequence VASNVES (SEQ ID NO: 3);
   iii) VL-CDR3 comprises the amino acid sequence QQSTKVPWT (SEQ ID NO: 4);
   iv) VH-CDR1 comprises the amino acid sequence TNAMN (SEQ ID NO: 6);
   v) VH-CDR2 comprises the amino acid sequence RIRSKSNNYATYYAESVKD (SEQ ID NO: 7); and
   vi) VH-CDR3 comprises the amino acid sequence DGYY (SEQ ID NO: 8).

2. The bispecific antibody according to claim 1, which comprises a VL domain comprising the amino acid sequence of SEQ ID NO: 11 and a VH domain comprising the amino acid sequence of SEQ ID NO: 15.

3. The bispecific antibody according to claim 1, which comprises a VL domain comprising the amino acid sequence of SEQ ID NO: 19 and a VH domain comprising the amino acid sequence of SEQ ID NO: 20.

4. The bispecific antibody according to claim 1, which comprises a VL domain comprising the amino acid sequence of SEQ ID NO: 1 and a VH domain comprising the amino acid sequence of SEQ ID NO: 5.

5. The bispecific antibody according to claim 1, which comprises a VL domain comprising the amino acid sequence of SEQ ID NO: 9 and a VH domain comprising the amino acid sequence of SEQ ID NO: 10.

6. The bispecific antibody according to claim 1, which comprises a light chain sequence of SEQ ID NO: 21 and a heavy chain sequence of SEQ ID NO: 23.

7. The bispecific antibody according to claim 6, which comprises a VL domain comprising the amino acid sequence of SEQ ID NO: 26 and a VH domain comprising the amino acid sequence of SEQ ID NO: 28.

8. The bispecific antibody according to claim 1, which comprises murine, chimeric or humanized sequences.

9. The bispecific antibody according to claim 1, which binds CD20 with a Kd<$10^{-8}$ M and/or which binds CD95 with a Kd<$10^{-8}$ M.

10. A pharmaceutical composition comprising the bispecific antibody according to claim 1 and a pharmaceutically acceptable carrier or excipient.

* * * * *